US012746269B2

(12) United States Patent
Li et al.

(10) Patent No.: US 12,746,269 B2
(45) Date of Patent: Sep. 29, 2026

(54) CYCLIC PEPTIDE COMPOUNDS AND METHODS OF USE

(71) Applicants: Fengqiao Li, Chapel Hill, NC (US); Michael Peter Vitek, Efland, NC (US)

(72) Inventors: Fengqiao Li, Chapel Hill, NC (US); Michael Peter Vitek, Efland, NC (US); Yuchen Chen, Chapel Hill, NC (US)

(73) Assignees: Fengqiao Li; Michael Peter Vitek

( * ) Notice: Subject to any disclaimer, the term of this patent is extended or adjusted under 35 U.S.C. 154(b) by 961 days.

(21) Appl. No.: 18/064,677

(22) Filed: Dec. 12, 2022

(65) Prior Publication Data

US 2023/0210939 A1 Jul. 6, 2023

Related U.S. Application Data

(63) Continuation of application No. PCT/US2021/039021, filed on Jun. 25, 2021.

(60) Provisional application No. 63/044,493, filed on Jun. 26, 2020.

(51) Int. Cl.
*A61K 38/12* (2006.01)
*A61P 9/10* (2006.01)

(52) U.S. Cl.
CPC ................ *A61K 38/12* (2013.01); *A61P 9/10* (2018.01)

(58) Field of Classification Search
CPC .......... A61K 38/00; A61K 38/12; A61K 9/00; A61K 9/0019; A61K 9/19; A61P 9/10; A61P 25/00; C07K 14/775; C07K 7/08
See application file for complete search history.

(56) References Cited

U.S. PATENT DOCUMENTS

| | | | | |
|---|---|---|---|---|
| 7,947,645 | B2 | 5/2011 | Vitek et al. | |
| 8,034,762 | B2 * | 10/2011 | Vitek | A61P 43/00 530/324 |
| 9,809,640 | B2 | 11/2017 | Vitek et al. | |
| 2010/0144627 | A1 | 6/2010 | Vitek et al. | |

FOREIGN PATENT DOCUMENTS

| | | | |
|---|---|---|---|
| JP | 2008511680 | A | 4/2008 |
| JP | 2011526922 | A | 10/2011 |
| WO | 20060029028 | A2 | 3/2006 |
| WO | 20080080082 | A2 | 7/2008 |
| WO | 20110085110 | A2 | 7/2011 |

OTHER PUBLICATIONS

D'Souza, C. et al., "Using the MCoTI-II cyclotide scaffold to design a stable cyclic peptide antagonist of SET, a protein overexpressed in human cancer", Biochemistry, 2016, vol. 55, pp. 396-405.
Chen, S. et al., "TREM2 activation attenuates neuroinflammation and neuronal apoptosis via PI3K/Akt pathway after intracerebral hemorrhage in mice", Journal of Neuroinflammation, May 28, 2020, vol. 17, 1 68, pp. 1-16.
ISA/KR; International Search Report and Written Opinion for International Patent Application No. PCT/US2021/039021 dated Oct. 21, 2021, 11 pages.
WIPO; International Preliminary Report on Patentability for International Patent Application No. PCT/US2021/039021 dated Dec. 13, 2022, 5 pages.
EPO, Extended European Search Report for corresponding European Patent Application No. 21829958.4 dated Jul. 2, 2024, 7 pages.

* cited by examiner

*Primary Examiner* — D. L. Jones
(74) *Attorney, Agent, or Firm* — NK Patent Law

(57) ABSTRACT

Cyclic peptide compounds are provided having the general formula (I) shown below. The cyclic peptide compounds are also provided for use in the preparation of a pharmaceutical composition for preventing and/or treating stroke, and related conditions or diseases. Experimental data indicate that the cyclic peptide compounds can have a preventive and/or therapeutic effect on stroke, and related conditions/diseases.

(SEQ ID NO: 1)

(I)

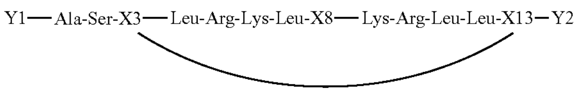

10 Claims, No Drawings

Specification includes a Sequence Listing.

CYCLIC PEPTIDE COMPOUNDS AND METHODS OF USE

CROSS-REFERENCE TO RELATED APPLICATIONS

This application is a continuation of international patent application no. PCT/US2021/039021, filed on Jun. 25, 2021, which claims the benefit of priority of U.S. provisional patent application No. 63/044,493, filed on Jun. 26, 2020, the disclosures of which are each incorporated herein by this reference in their entireties.

SEQUENCE LISTING

The instant application contains a Sequence Listing which has been submitted electronically in Xml file format and is hereby incorporated by reference in its entirety. Said XML copy, created on Mar. 3, 2023, is named 1185_2_UTIL_SL.xml and is 65,591 bytes in size.

FIELD OF INVENTION

The present invention relates to the field of medicine, specifically to cyclic peptide compounds and their use in the treatment and/or prevention of neurodegeneration and brain inflammation as a result of stroke and/or other inflammatory diseases.

BACKGROUND

Cerebral stroke, also known as "stroke", is an acute cerebrovascular disease. Related medical research has shown that stroke is a group of diseases that cause brain tissue damage due to sudden rupture of blood vessels in the brain or impaired blood flow into the brain due to blockage of blood vessels, which is known as hemorrhagic or ischemic stroke, respectively. Stroke has the characteristics of high morbidity, high mortality, and high disability rate.

Treatment of stroke includes thrombolysis, antiplatelet therapy, early anticoagulation, and neuroprotection. Non-specific treatment includes antihypertensive therapy, blood glucose management, management of cerebral edema and intracranial hypertension. However, different types of stroke have different treatments. Due to the lack of effective treatments, prevention is currently considered the best measure.

Therefore, there remains an unmet need to develop drugs that have improved therapeutic and/or preventive effects on neurodegeneration and brain inflammation associated with stroke.

SUMMARY

The inventors have discovered that a series of cyclic peptides based on an apolipoprotein-E peptide (apoE-peptide) have excellent neuroprotective and/or anti-inflammatory effects for the treatment and/or prevention of stroke and/or other inflammatory diseases.

In one aspect, the present invention provides a cyclic peptide compound having the structure of formula (I) below and the sequence of residues 1 through 13 of SEQ ID NO: 1:

(SEQ ID NO: 1)

(I)

Y1—Ala-Ser-X3—Leu-Arg-Lys-Leu-X8—Lys-Arg-Leu-Leu-X13—Y2 wherein:

X3 and X13 are independent amino acid residues selected from Cys, Glu, Asp, Lys, Orn, 2,4-Diaminobutyric Acid (Dab), 2,3-Diaminopropionic Acid (Dap), Ser, Gln, halogenated alanine, and their corresponding enantiomeric D-amino acids;

X8 is amino iso-butyric acid (Aib);

The symbol "⌣" represents a joining group comprised of a chemical bond between X3 and X13, wherein the chemical bond is selected from: —SS—, $—CH_2—S—CH_2—$, —CO—NH—, —CO—O—, $—CH_2—NH—$, $—(CH_2)n-$ (n=2-15), or $—(CH_2)_n—CH{=}CH—(CH_2)_n—$ (n=2-15); or the chemical bond is $—S—(CH_2)_n—R_1—(CH_2)_n—S—$, wherein $R_1$ is a hydrocarbon group, an aryl group or a heteroaryl group, n=1-3;

Y1 may be present or absent, and when present, Y1 is $R_2$—CO—, wherein $R_2$ is selected from: a hydrocarbon group, an aryl group or a heteroaryl group;

Y2 may be present or absent, and when present, Y2 is a carboxy-terminal group.

In one embodiment,

X13 is Cys, X8 is Aib, and X3 is Cys (SEQ ID NO: 2);

X13 is Cys, X8 is Aib, and X3 is D-Cys (SEQ ID NO: 3);

X13 is D-Cys, X8 is Aib, and X3 is Cys (SEQ ID NO: 4);

X13 is D-Cys, X8 is Aib, and X3 is D-Cys (SEQ ID NO: 5);

X13 is a Glu or Asp, X8 is Aib, and X3 is a Lys, Orn, Dab, or Dap (SEQ ID NO: 6);

X13 is a Lys, Orn, Dab, or Dap, X8 is Aib, and X3 is a Glu or Asp (SEQ ID NO: 7);

X13 is a Glu or Asp, X8 is Aib, and X3 is a D-Lys, D-Orn, D-Dab, or D-Dap (SEQ ID NO: 8);

X13 is a D-Glu or D-Asp, X8 is Aib, and X3 is a Lys, Orn, Dab, or Dap (SEQ ID NO: 9);

X13 is a D-Glu or D-Asp, X8 is Aib, and X3 is a D-Lys, D-Orn, D-Dab, or D-Dap (SEQ ID NO: 10);

X13 is a Lys, Orn, Dab, or Dap, X8 is Aib, and X3 is a D-Glu or D-Asp (SEQ ID NO: 11);

X13 is a D-Lys, D-Orn, D-Dab, or D-Dap, X8 is Aib, and X3 is a Glu or Asp (SEQ ID NO: 12);

X13 is a D-Lys, D-Orn, D-Dab, or D-Dap, X8 is Aib, and X3 is a D-Glu or D-Asp (SEQ ID NO: 13);

X13 is halogenated alanine, X8 is Aib, and X3 is Cys (SEQ ID NO: 14);

X13 is halogenated D-alanine, X8 is Aib, and X3 is Cys (SEQ ID NO: 15); or

X13 is halogenated D-alanine, X8 is Aib, and X3 is D-Cys (SEQ ID NO: 16).

In one embodiment, Y1 is $R_2$—CO—, wherein $R_2$ is selected from: C1-C4 linear or branched alkyl, C2-C4 linear or branched alkenyl, C2-C4 alkynyl, a 5-10 membered aryl group, or a 5-10 membered heteroaryl group selected from O, S and N.

In one embodiment, Y1 is selected from acetyl, picolinyl, or pyrazinecarbonyl.

In one embodiment, the —COOH ends of the amino acids represented by Y2 and X13 form a structure selected from $—CH_2—OH$ or —COR, where R is selected from $—NH_2$, H, $-CH_3$, $-OCH_3$, $-OC_2H_5$, —NH—OH, $-NH-CH_3$, $-N(CH_3)_2$, $-NH-C_2H_5$, $-NH-C_6H_5$ or $-NH-C_6H_4-NO_2$.

In one embodiment, $R_2$ is phenyl or cyclopropyl.

In one embodiment, the cyclic peptide compound is:

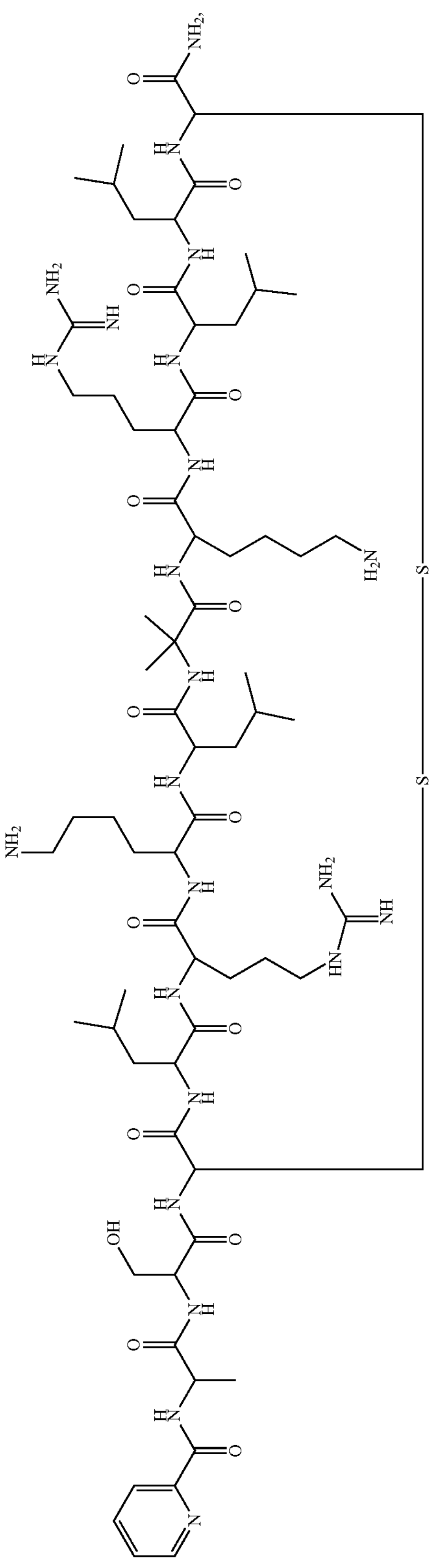
(SEQ ID NO: 18, Compound 1)
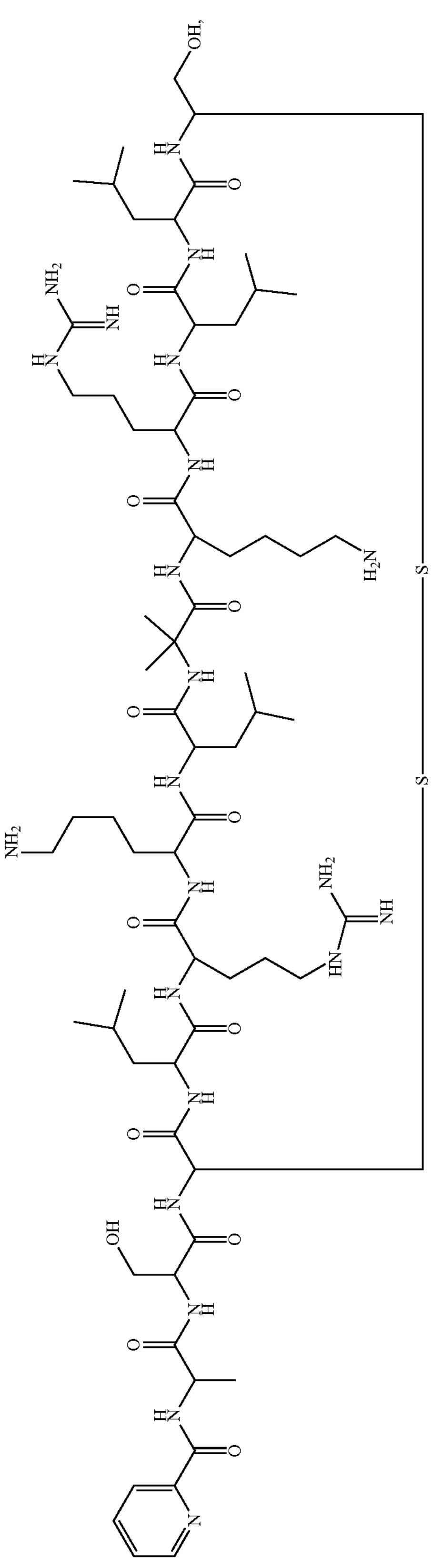
(SEQ ID NO: 19, Compound 2)

-continued
(SEQ ID NO: 20, Compound 3)
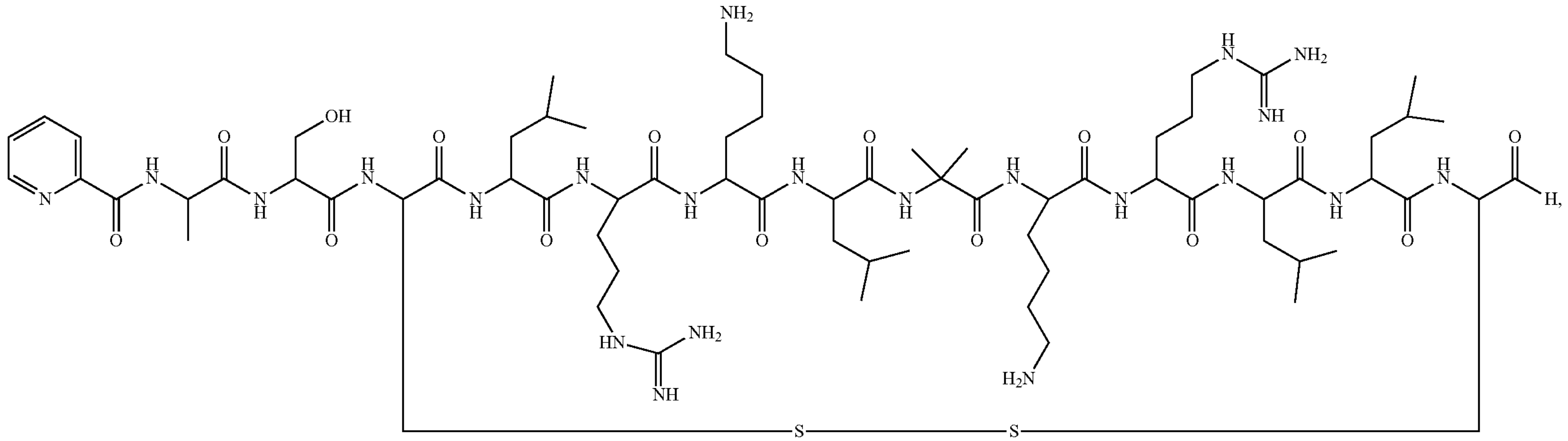
(SEQ ID NO: 22, Compound 4)
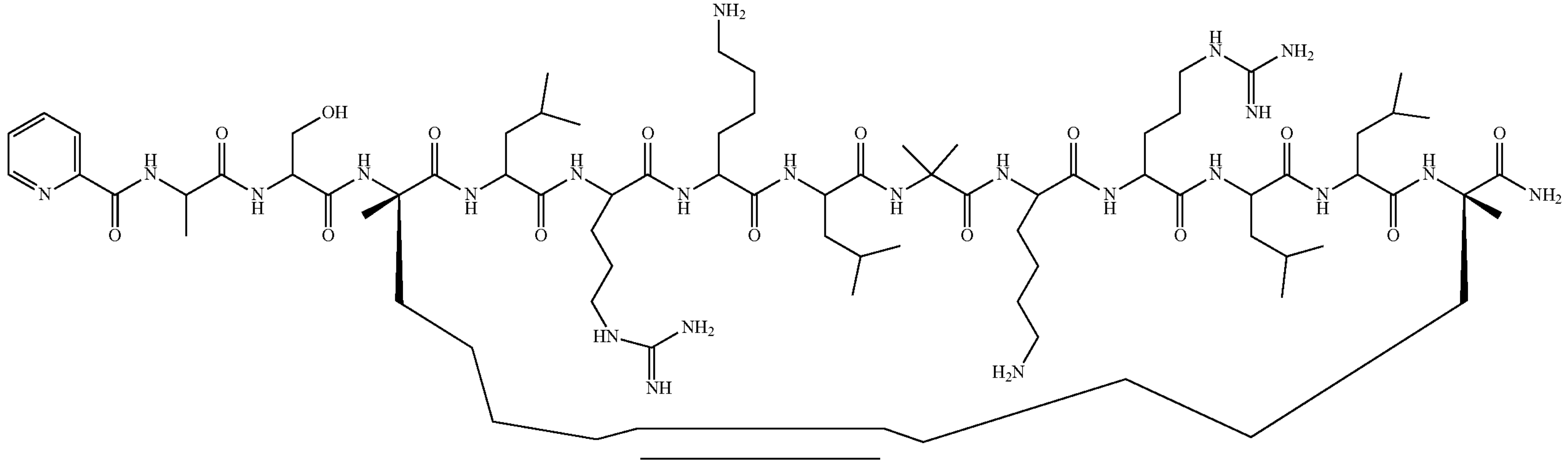
or -continued
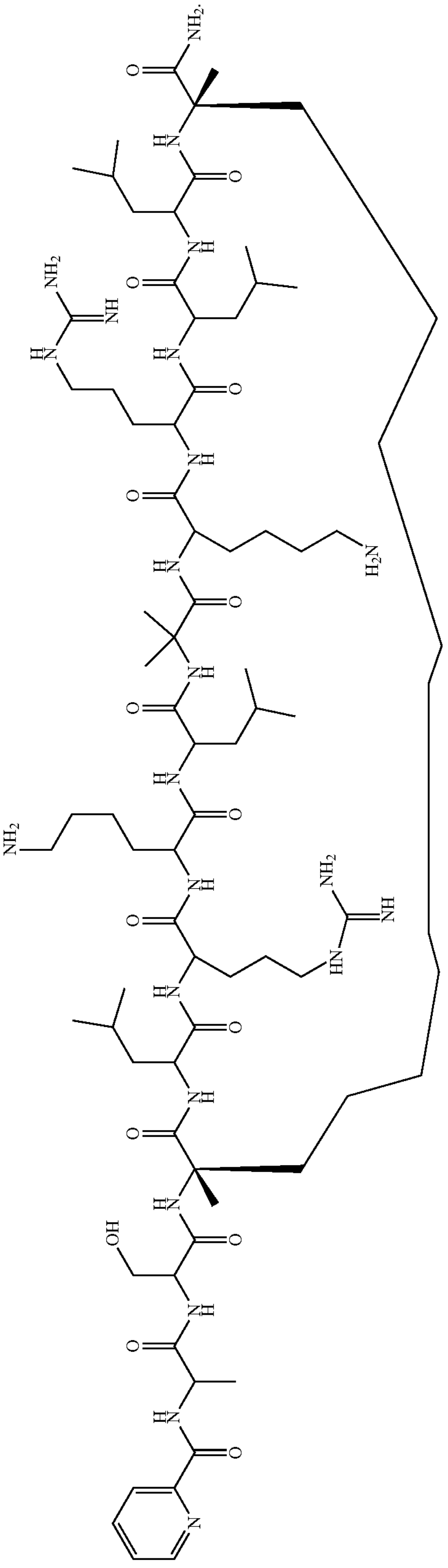
(SEQ ID NO: 22, Compound 5)

In one aspect, the present invention provides a cyclic peptide compound having the structure of formula (II) and amino acid sequence of residues 1 through 13 of (SEQ ID NO: 17): Y1-Ala-Ser-X3-Leu-Arg-Lys-Leu-X8-Lys-Arg-Leu-Leu-X13-Y2 wherein:

X3, X8, and X13 are independent amino acid residues selected from Cys, Glu, Asp, Lys, Orn, 2,4-Diaminobutyric Acid (Dab), 2,3-Diaminopropionic Acid (Dap), Ser, Gln, halogenated alanine, and their corresponding enantiomeric D-amino acids, or amino iso-butyric acid (Aib);

The symbol "‿" represents a joining group comprised of a chemical bond between X3 and X8 or X8 and X13, wherein the chemical bond is selected from: —SS—, $—CH_2—S—CH_2—$, —CO—NH—, —CO—O—, $—CH_2—NH—$, $—(CH_2)n-$ (n=2-15), or $—(CH_2)_n—CH{=}CH—(CH_2)_n—$ (n=2-15); or the chemical bond is $—S—(CH_2)_n—R_1—(CH_2)_n—S—$, wherein $R_1$ is a hydrocarbon group, an aryl group or a heteroaryl group, n=1-3;

Y1 may be present or absent, and when present, Y1 is $R_2—CO—$, wherein $R_2$ is selected from: a hydrocarbon group, an aryl group or a heteroaryl group;

Y2 may be present or absent, and when present, Y2 is a carboxy-terminal group.

In another aspect, embodiments of the invention provide for the use of one or more cyclic peptide compounds of the invention in the preparation of a pharmaceutical composition for the prevention and/or treatment of stroke and/or related diseases.

In one embodiment, the related disease is an inflammatory disease, a neurodegenerative disease, or a peripheral nerve-damaging disease.

In one embodiment, the related disease is a neuroinflammatory disease.

In one embodiment, the related disease is one or more of cerebral hemorrhage, cerebral ischemia, cerebral trauma, spinal cord injury, multiple sclerosis, Parkinson's disease, and Alzheimer's disease.

In one embodiment, the related disease is one or more of sepsis, colitis, osteoarthritis and rheumatoid arthritis.

In another aspect, embodiments of the present invention provide a cyclic peptide compound for preventing and/or treating stroke and/or related diseases.

In another aspect, embodiments of the present invention provide a method for preventing and/or treating stroke and/or related diseases, comprising administering to a subject in need thereof an effective amount of the cyclic peptide compound of the present invention.

In one embodiment, the related disease is an inflammatory disease, a neurodegenerative disease, and/or a peripheral nerve-damaging disease.

In one embodiment, the related disease is a neuroinflammatory disease.

In one embodiment, the related disease is one or more selected from the group consisting of cerebral hemorrhage, cerebral ischemia, multiple sclerosis, Parkinson's disease, and Alzheimer's disease.

In one embodiment, the related disease is one or more selected from the group consisting of sepsis, colitis, rheumatoid arthritis and osteoarthritis.

In one embodiment, the administration includes single administration or multiple administrations.

In one embodiment, the multiple administrations include a method of: once a day, twice a day, three times a day, once a week, twice a week, three times a week, four times a week, once every two weeks, or once a month.

In one embodiment, the effective amount is 0.01-1.0 mg/kg body weight.

In one embodiment, the subject is a mammal, preferably a primate, more preferably a human.

In another aspect, embodiments of the present invention provide a pharmaceutical composition comprising the cyclic peptide compound of the present invention.

In one embodiment, the pharmaceutical composition further includes pharmaceutically acceptable excipients.

In one embodiment, the pharmaceutically acceptable excipients include one or more of excipients, disintegrants, diluents, binders, solvents, co-solvents, lubricants, pH adjustment agents, buffers, preservatives, dispersants, suspending agents, ointment bases, emulsifiers, emollients, penetration enhancers, surfactants, propellants, flavoring agents, sweeteners, and/or drug release modifiers.

In one embodiment, the pharmaceutically acceptable excipients include excipients, pH adjusters, buffers, solvents, and/or binders.

In one embodiment, the excipient comprises mannitol.

In one embodiment, the pH adjusting agent includes one or more of hydrochloric acid, acetic acid, tartaric acid, citric acid, and/or sodium hydroxide.

In one embodiment, the buffering agent includes one or more of citric acid alkali metal salt solution and phosphoric acid alkali metal salt solution, preferably sodium citrate salt solution and/or sodium phosphate salt solution.

In one embodiment, the solvent includes one or more of physiological saline and/or glucose solution.

In one embodiment, the binder comprises sodium carboxymethyl cellulose.

In one embodiment, the pharmaceutical composition may be one or more dosage forms selected from lyophilized powder, injection, water injection, sustained release agent and/or spray.

Experiments have confirmed that the cyclic peptide compound of the present invention can have a stable structure, low biological toxicity, and excellent therapeutic and/or preventive effects on stroke and/or related diseases.

DETAILED DESCRIPTION

The invention will now be described in detail with reference to representative embodiments of the invention. These embodiments are merely exemplary and should not be construed as limiting the scope of the present invention in any way. On the contrary, the invention is intended to cover all alternatives, modifications, and equivalents within the scope of the invention as defined by the claims.

Unless otherwise indicated, technical and scientific terms used herein have the same meaning as commonly understood by those of ordinary skill in the art to which this invention belongs.

Definition

(i) General

As used herein, the terms "comprising", "including", "having", or "containing" are herein used interchangeably and are intended as being non-exclusive, i.e., understood to imply the inclusion of the stated elements or group of elements, but not the exclusion of any other elements or group of elements. For example, a composition, mixture, process, method, article, or apparatus comprising a series of components is not limited to those components, and it may include other components not expressly listed as the composition, mixture, process, method, article, or apparatus.

Furthermore, the indefinite articles "a" and "an" preceding an element or component of the invention are not intended to limit the number of occurrences of the element or component. Therefore, "a" and "an" should be understood to include one or at least one, and unless the number is explicitly singular, the singular form of the element or component also includes the plural form.

(ii) The Cyclic Peptide Compound of the Present Invention

In one embodiment, the cyclic peptide compound of the present invention may have a general structure of formula (I) and amino acid sequence of residues 1 through 13 of SEQ ID NO: 1 as shown below:

(SEQ ID NO: 1)

(I)

Y1—Ala-Ser-X3—Leu-Arg-Lys-Leu-X8—Lys-Arg-Leu-Leu-X13—Y2

In the above structural formula (I), Leu, Arg, Lys, Ser, His, and Ala are the three-letter abbreviations of amino acids, respectively representing leucine, arginine, lysine, serine, histidine, and alanine. Those skilled in the art understand that in the peptide chain structure, the above-mentioned amino acids are in the form of amino acid residues. In the present invention, unless otherwise specified, the amino acids included in the peptide chain structure refer to amino acid residues.

Unless otherwise specified, two adjacent amino acids are connected by an amide bond (—CO—NH—), also known as a peptide bond. For example, -Ala-Ser- means that the alanine residue is connected to the serine residue, and the two are connected by an amide bond, which in this case, because Ala and Ser and amino acids, is also known as a peptide bond.

In the above structural formula (I), Leu, Arg, Lys, Ser, His, and Ala may represent L-amino acids.

In the above structural formula (I), "⌣" represents a chemical bond between the two, non-adjacent amino acid residues in the peptide construct, X3 and X13, thereby forming a cyclic peptide structure compound.

In other embodiments, a chemical bond, "⌣" may be present between X3 and X8 or between X8 and X13 of structural formula (II), (SEQ ID NO: 17). Therefore, in one or more embodiments of the present invention, unless otherwise specified, the position of the chemical bond "⌣" may be changed in one peptide versus another peptide.

Chemical bonds may be used to form the cyclic peptides. These chemical bonds are abbreviated by the symbol "⌣" and include, but are not limited to, —SS—, —$CH_2$—S—$CH_2$—, —CO—NH—, —$(CH_2)$n- (n=2-15), and —$(CH_2)$n-CH═CH—$(CH_2)$n- (n=2-15), —S—$(CH_2)$n-$R_1$—$(CH_2)$n-S— (wherein $R_1$ is a hydrocarbon group, aryl group and heteroaryl group, n=1-3), or —CO—$CH_2$—S—$CH_2$—. In one embodiment, the chemical bond "⌣" is —SS— (a disulfide group or a disulfide bridge).

In the present invention, the term "hydrocarbyl" should be understood as preferably comprising a C1-C6-alkyl, C2-C6-alkenyl, C2-C6-alkynyl, C3-C6-cycloalkyl, or 3- to 7-membered heterocycloalkyl.

The term "C1-C6-alkyl" is to be understood as preferably meaning having 1, 2, 3, 4, 5 or 6 saturated monovalent hydrocarbon group, straight-chain or branched-chain carbon atoms, e.g., methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methyl amylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl or their isomers. In particular, said group having 1, 2, 3 or 4 carbon atoms ("C1-C4-alkyl") such as methyl, ethyl, propyl, butyl, isopropyl, isobutyl group, sec-butyl, tert-butyl, more particularly, a group having 1, 2, or 3 carbon atoms ("C1-C3-alkyl"), e.g., methyl, ethyl, n-propyl or isopropyl.

The term "C2-C6-alkenyl" is to be understood as preferably meaning a linear or branched divalent hydrocarbon chain comprising one or more double bonds and having 2, 3, 4, 5 or 6 carbon atoms, especially including 2 or 3 carbon atoms ("C2-C3-alkenyl group"), it should be understood that, in the case where the alkenyl group contains more than one double bond, the double bonds may be isolated or conjugated to each other. The alkenyl group is, for example, vinyl, allyl, (E)-2-methyl vinyl, (Z)-2-methyl vinyl, homoallyl, (E)-but-2-enyl, (Z)-but-2-enyl, (E)-but-1-enyl, (Z)-but-1-enyl, pent-4-enyl, (E)-pent-3-ene group, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hexyl-3-alkenyl group, (E)-hexyl-2-alkenyl group, (Z)-hexyl-2-alkenyl group, (E)-hexyl-1-alkenyl group, (Z)-hexanoic-1-ene, isopropenyl, 2-methylprop-2-enyl, 1-methylprop-2-enyl, 2-methylprop-1-enyl, (E)-1-methylpropan-1-alkenyl, (Z)-1-methyl-prop-1-enyl, 3-methylbut-3-enyl, 2-methylbut-3-enyl, 1-methylbut-3-ene, 3-methylbut-2-enyl, (E)-2-methylbut-2-enyl, (Z)-2-methylbut-2-enyl, (E)-1-methyl methylbut-2-alkenyl group, (Z)-1-methylbut-2-alkenyl group, (E)-3-methylbut-1-alkenyl group, (Z)-3-methylbut-1-alkenyl, (E)-2-methylbut-1-enyl, (Z)-2-methylbut-1-enyl, (E)-1-methylbut-1-enyl, (Z)-1-methylbut-1-enyl, 1,1-dimethyl-prop-2-enyl, 1-ethylpropyl-1-enyl, 1-propyl vinyl, 1-isopropyl vinyl, 4-methylpent-4-enyl, 3-methylpent-4-enyl, 2-methylpent-4-enyl, 1-methylpent-4-enyl, 4-methylpent-3-en alkenyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methyl pentyl 2-enyl, (Z)-4-methylpent-2-enyl, (E)-3-methylpent-2-enyl, (Z)-3-methylpent-2-Alkenyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methyl pentyl-1-alkenyl group, (Z)-3-methylpent 1-alkenyl group, (E)-2-methyl-pent-1-alkenyl group, (Z)-2-methyl-pent-1-alkenyl group, (E)-1-methyl-pent-1-alkenyl group, (Z)-1-methyl-pent-1-enyl, 3-ethylbutyrate-3-enyl, 2 ethylbutyrate-3-alkenyl, 1-ethylbut-3-enyl, (E)-3-ethylbut-2-enyl, (Z)-3-ethylbut-2-enyl, (E)-2-ethylbutan-2-alkenyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-alkenyl, (Z)-1-ethylbutyrate-1-enyl, 2-propyl-prop-2-enyl, 1-propyl-prop-2-enyl, 2-isopropyl-prop-2-alkenyl, 1-isopropylprop-2-enyl, (E)-2-propylprop-1-enyl, (Z)-2-propylprop-1-enyl, (E)-1-propyl-prop-1-alkenyl group, (Z)-1-propyl-prop-1-alkenyl group, (E)-2-isopropyl-prop-1-alkenyl group, (Z)-2-isopropyl-prop-1-enyl, (E)-1-isopropylprop-1-enyl, (Z)-1-isopropylprop-1-enyl, (E)-3,3-dimethyl-prop-1-enyl, (Z)-3,3-dimethylprop-1-enyl, 1-(1,1-dimethylethyl) vinyl, but-1,3-dienyl, Pent-1,4-dienyl, hex-1,5-dienyl or methylhexadienyl. In particular, the group is vinyl or allyl.

The term "C2-C6-alkynyl" is to be understood as preferably meaning a linear or branched divalent hydrocarbon chain comprising one or more triple bonds and containing 2, 3, 4, 5 or 6 carbon atoms, especially including 2 or 3 carbon atoms ("C2-C3-alkynyl group"). The C2-C6-alkynyl group is for example ethynyl, prop-1-ynyl, prop-2-ynyl, but-1-ynyl, but-2-ynyl, but-3-alkynyl group, Pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, -methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1methylpent-3-ynyl, 4-methylpent-2-ynyl, 1-methylpentyl-2-ynyl, 4-methylpent-1-ynyl, 3methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1, 1-dimethylbut-3-ynyl, 1,1dimethylbut-2-ynyl or 3,3-dimethylbut-1-ynyl. In particular, the alkynyl group is ethynyl, prop-1-ynyl or prop-2-ynyl.

The term "$C_3$-$C_6$-cycloalkyl" is to be understood as meaning a saturated monovalent monocyclic hydrocarbon ring containing 3, 4, 5 or 6 carbon atoms ("$C_3$-$C_6$-cycloalkyl"). The $C_3$-$C_6$-cycloalkyl group is for example cyclopropyl, cyclobutyl, cyclopentyl or cyclohexyl rings.

The term "3 to 7-membered heterocycloalkyl" is to be understood as meaning a saturated monovalent monocyclic or bicyclic hydrocarbon ring which contains 2, 3, 4, 5 or 6 carbon atoms and one or more groups selected from C(═O), O, S, S(═O), $S(═O)_2$. $NR^a$ group containing a hetero atom, wherein Ra represents a hydrogen atom, $C_1$-$C_6$-alkyl- or halogenated —$C_1$-$C_6$-alkyl-group; the heterocycloalkyl (if present) is connected to the rest of the molecule through either a nitrogen atom or a carbon atom.

In particular, the 3- to 7-membered heterocyclic group may contain 2, 3, 4 or 5 carbon atoms and one or more hetero atoms, the above groups ("3- to 6-membered heterocycloalkyl group"), more particularly said heterocycloalkyl may contain 4 or 5 carbon atoms and one or more of the heteroatom-containing radicals ("5- to 6-membered heterocycloalkyl"), wherein the 3- to 7-membered heterocycloalkyl, -two groups of adjacent atoms form an aryl group—or a heteroaryl group—that are optionally substituted.

In particular, the heterocycloalkyl group may be, for example, but not limited to: a 4-membered ring, such as azetidine, or oxetanyl; or a 5-membered ring, such as tetrahydrofuranyl, metadioxane amyl (dioxolinyl), pyrrolidinyl, imidazolidinyl, pyrazolidinyl, or pyrrolinyl; or a 6-membered ring, such as tetrahydropyranyl, piperidinyl, morpholinyl, dithianyl, sulfur substituted morpholinyl, piperazinyl or trithianyl; or a 7-membered ring, such as diazacycloheptane rings. Optionally, the heterocycloalkyl group may be benzo-fused.

The term "aryl" is understood to mean preferably a monovalent aromatic or partially aromatic monocyclic, bicyclic or tricyclic hydrocarbon ring having 6, 7, 8, 9, 10, 11, 12, 13 or 14 carbon atoms ("$C_6$-$C_{14}$-aryl group"), in particular having 6 ring carbon atoms ("$C_6$-aryl group") such as phenyl; or biphenyl, or having 9 ring carbon atoms, ("$C_9$-aryl group"), for example, indanyl or indenyl, or having 10 ring carbon atoms ("$C_{10}$-aryl group"), for example, tetrahydronaphthyl, dihydronaphthyl or naphthyl, or having 13 ring carbon atoms ("$C_{13}$-aryl group"), for example, a fluorenyl group, or having 14 ring carbon atoms ("$C_{14}$-aryl groups") such as anthracene group, wherein said aryl-group contains two adjacent atoms to form a 3- to 7-membered heterocycloalkyl groups, where the groups are optionally substituted.

The term "heteroaryl" is understood to mean preferably a monovalent monocyclic, bicyclic or tricyclic aromatic ring system having 5, 6, 7, 8, 9, 10, 11, 12, 13, or 14 rings atom ("5- to 14-membered heteroaryl"), especially 5 or 6 or 9 or 10 carbon atoms, and it contains at least one heteroatom which may be the same or different (the heteroatom is for example oxygen, nitrogen or sulfur), and, in addition, may be benzo-fused in each case. In particular, the heteroaryl group is selected from thienyl, furyl, pyrrolyl, oxazolyl, thiazolyl, imidazolyl, pyrazolyl, isoxazolyl, isothiazolyl, oxadiazolyl, triazolyl, thio-oxadiazolyl, thiazole-4H-pyrazolyl (thia-4H-pyrazolyl) etc., and benzo derivatives thereof, e.g. benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and their benzene derivatives, such as quinolinyl, quinazolinyl, isoquinolinyl, etc.; or azocinin (azocinyl), indazinyl, purinyl, etc. and/or their benzo derivatives; or cinnolinyl, phthalide azinyl, quinazolinyl, quinoxalinyl, naphthpyridinyl, pteridinyl, carbazolyl, acridinyl, phenazinyl, phenothiazinyl, phenoxazinyl, xanthene or oxepin-yl (oxepinyl) and the like.

In general and unless otherwise stated, the heteroaryl or heteroarylene group includes all possible isomeric forms thereof, such as its positional isomers. Thus, for some illustrative non-limiting examples, the term pyridyl or pyridinylene includes pyridin-2-yl, pyridin-2-radicals, pyridin-3-yl, pyridin-3-radicals, pyridin-4-yl and pyridin-4-radicals; or, the term thienyl or thienylene includes thien-2-yl, thien-2-radicals, thien-3-yl and thien-3-radicals.

In one embodiment, $R_1$ is phenyl or cyclopropyl.

In one aspect of the present invention, n- may independently be selected from the representative 1-3 integer including 1, 2 or 3. Accordingly, in one embodiment, the respective chemical bond "" is —S—$CH_2$-phenyl-$CH_2$—S— or —S—$CH_2$-cyclopropyl-$CH_2$—S—.

In one aspect of the present invention, the amino terminal portion of Y1 and the amino acid to which Y1 is connected may contain an $R_2$—CONH— structure. In one embodiment, Y1 may be present or absent, and when present, Y1 is $R_2$—CONH—, where $R_2$ is selected from: hydrocarbyl, aryl, or heteroaryl.

For example, in the structure of the cyclic peptide shown below, Y1 is the part indicated by a dotted and dashed ellipse, specifically picolinyl:

(SEQ ID NO: 18, Compound 1)

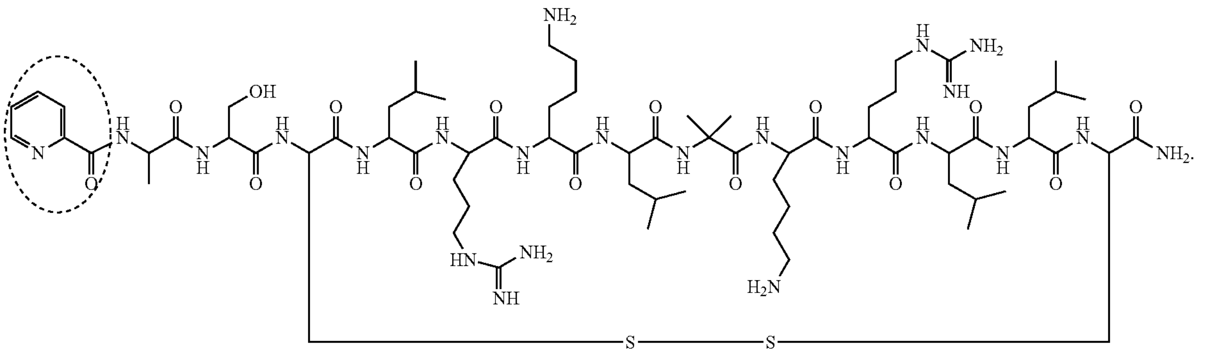

In one aspect of the present invention, the amino acid residues connected to Y2 can form a peptide amine, peptide alcohol, peptide aldehyde, peptide ketone, peptide acid, peptide methyl ester, peptide ethyl ester, peptide ketone, peptide hydroxamic acid, or peptide structures such as amine, peptide dimethylamine, peptide ethylamine, peptide aniline or peptide p-nitroaniline.

For example, in the structure of the cyclic peptide shown below, (SEQ ID NO: 21, Compound 3)

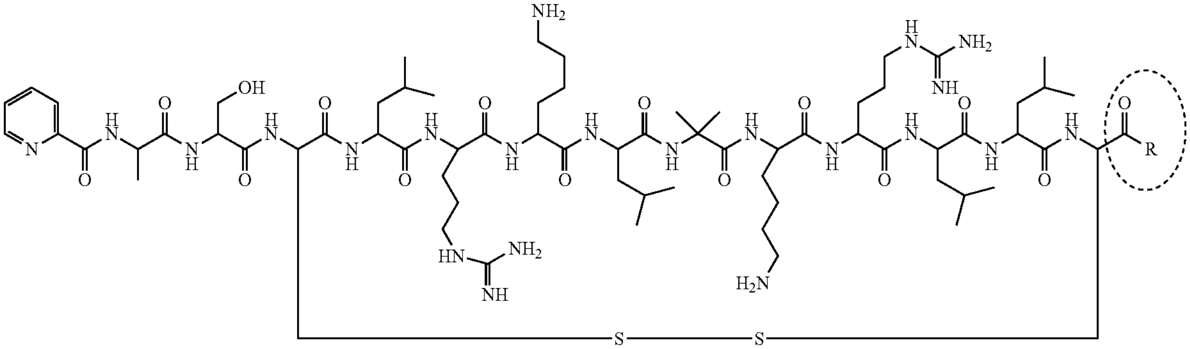

the carboxyl terminus of Y2 and its connected cysteine form —COR structure (shown by the dotted circle), where R is selected from —$NH_2$, H, —$CH_3$, —$OCH_3$, —$OC_2H_5$, —NH—OH, —NH—$CH_3$, —$N(CH_3)_2$, —NH—$C_2H_5$, —NH—$C_6H_5$ or —NH—$C_6H_4$—$NO_2$.

In a specific embodiment, in the structure of the cyclic peptide shown below, (SEQ ID NO: 18, Compound 1)

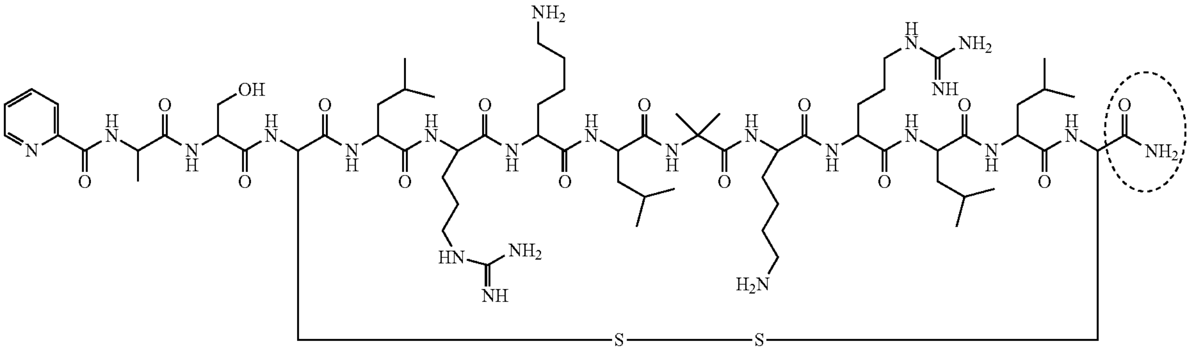

the carboxyl terminus of cysteine attached to Y2 forms a peptide amide, the structure of —$CONH_2$.

Or, in the structure of the cyclic peptide shown below, the carboxyl terminus of the cysteine to which Y2 is connected forms a structure of peptide alcohol, —$CH_2OH$:

(SEQ ID NO: 19, Compound 2)

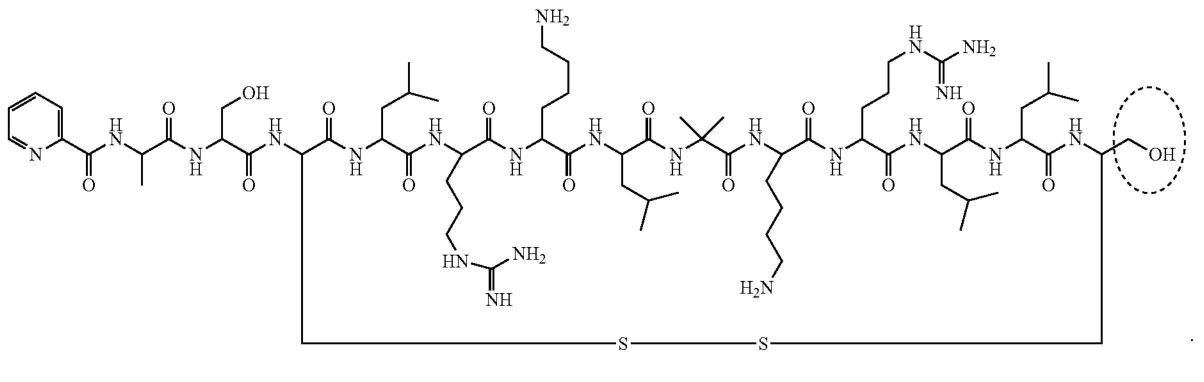

Therefore, in one embodiment, the —COOH ends of the amino acids represented by Y2 and X13 form a structure selected from: —$CH_2OH$ or —COR, where R is selected from —$NH_2$, H, —$CH_3$, —$OCH_3$, —$OC_2H_5$, —NH—OH, —NH—$CH_3$, —$N(CH_3)_2$, —NH—$C_2H_5$, —NH—$C_6H_5$ or —NH—$C_6H_4$—$NO_2$.

In one aspect of the present invention, if the chemical structural formula of the cyclic peptide compound of the present invention is inconsistent with the simplified structural formula, the simplified structural formula shall prevail. For example, if the following chemical structural formula of Compound 1 shown below:

(SEQ ID NO: 18, Compound 1)

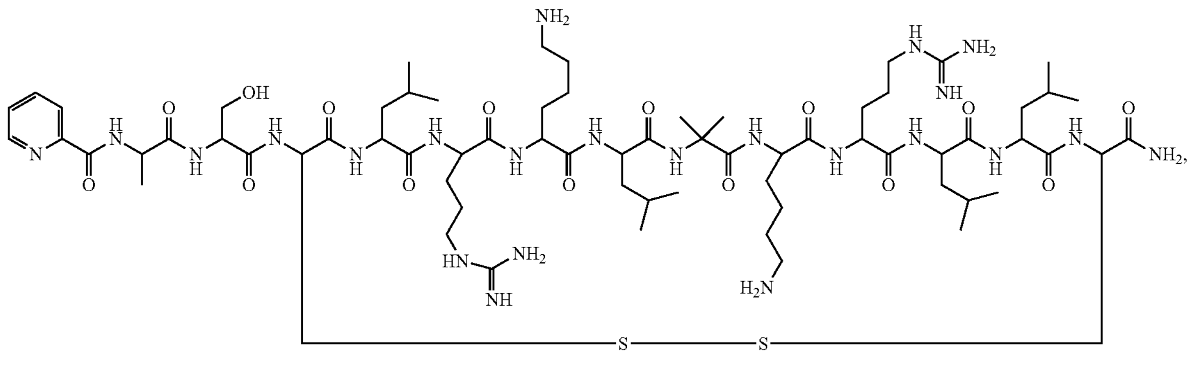

Is inconsistent with the simplified structural formula of Compound 1: picolinyl-Ala-Ser-cyclo[Cys-LRKL-Aib-KRLL-Cys]-$NH_2$ (SEQ ID NO: 18), formula $C_{70}H_{123}N_{23}O_{15}S_2$, the simplified formula shall prevail.

(iii) Method of Preparing the Cyclic Peptide Compound of the Present Invention The following discussion provides principles for obtaining the cyclic peptide compounds of the present invention and gives details of some methods available for preparing the cyclic peptide compounds of the present invention. However, the discussion is not intended to define or limit the scope of reactions or reaction sequences that can be used in the preparation of cyclic peptide compounds of the invention. The cyclic peptide compounds of the present invention can be prepared by the steps and techniques disclosed in the Examples section herein below and known organic synthesis techniques.

Methods known to those of ordinary skill in the art can be confirmed through various reference books and published data. Detailed description of the available reactants in the synthesis of the compounds of the present invention are available, or provided in references described in the literature and appropriate reference books including, for example, "Practical Synthetic Organic Chemistry", John Wiley & Sons, Inc., New York 2011; and the S R Sandler et al., "Organic Functional Group Preparations", 2nd Ed, Academic Press, New York, 1983; the H. O. House, "Modem Synthetic Reactions", 2nd Ed., WA Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structures", 4th Ed, Wiley.—Interscience, New York, 1992. A detailed description of the synthesis of reactants that can be used in the preparation of the compounds of the invention or other suitable reference books and monographs that provide references to the literature describing the preparation methods include, for example, Fuhrhop, J. and Penzlin G. "Organic Synthesis: Concepts, Methods, Starting Materials"; Second, Revised and Enlarged Edition (1994) John Wiley & Sons ISBN: 3-527-29074-5; Hoffman, RV "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; Otera, J. (editor) "Modern Carbonyl Chemistry" (2000) Wiley-VCH, ISBN: 3-527-29871-1; Patai, S. "Guide to The Chemistry of Functional Groups" (1992) Interscience ISBN: 0-471-93022-9; Quin, L. D. et al., "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C. "Intermediate Organic Chemistry" 2nd Edition (1993) Wiley-Interscience, ISBN: 0-471-57456-2; "Ullmann's Encyclopedia: Industrial Organic Chemicals: Starting Materials and Intermediates" (1999) John Wiley & Sons, ISBN: 3-527-29645-X-, in Volume. 8 "Organic Reaction" (1942-2000) John Wiley & Sons, in over 55 Volumes; and "Chemistry of Functional Groups" John Wiley & Sons, in 73 Volumes.

In summary, the compounds used in the reactions described herein can be prepared from commercially available chemical reagents and/or compounds described in the chemical literature according to organic synthesis techniques known to those skilled in the art. "Commercially available chemical reagents" can be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire UK), BDH Inc. (Toronto, Canada), Bionet (Cornwall, UK), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall UK), Lancaster Synthesis (Windham NH), Maybridge Chemical Co. Ltd. (Cornwall UK), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, NJ), TCI America (Portland Oreg.), Trans World Chemicals, Inc. (Rockville Md.) and Wako Chemicals USA, Inc. (Richmond Va.).

Specific reactants and similar reactants can be confirmed by an index of known chemical reagents (obtained from most public or university libraries) prepared by the Chemical Abstracts Service of the American Chemical Society or through online databases. Chemical reagents that are known but not commercially available in the catalog can be prepared by custom chemical reagent synthesizers, many of which are standard chemical reagent providers (such as those above) that provide custom synthesis services.

The amino acid residues connected to Y2 can form peptide amine, peptide alcohol, peptide aldehyde, peptide ketone, peptide acid, peptide methyl ester, peptide ethyl ester, peptide ketone, peptide hydroxamic acid, peptide methylamine, and peptide dimethyl structures such as amine, peptide ethylamine, peptide aniline or peptide p-nitroaniline. The method for forming the amino acid residue to which Y2 is connected, to obtain the above terminal structure, is known to those skilled in the art.

For example, Compound 2 shown in the schematic below may be a cyclic peptide compound having the following peptide alcohol structure:

(SEQ ID NO: 19, Compound 2)

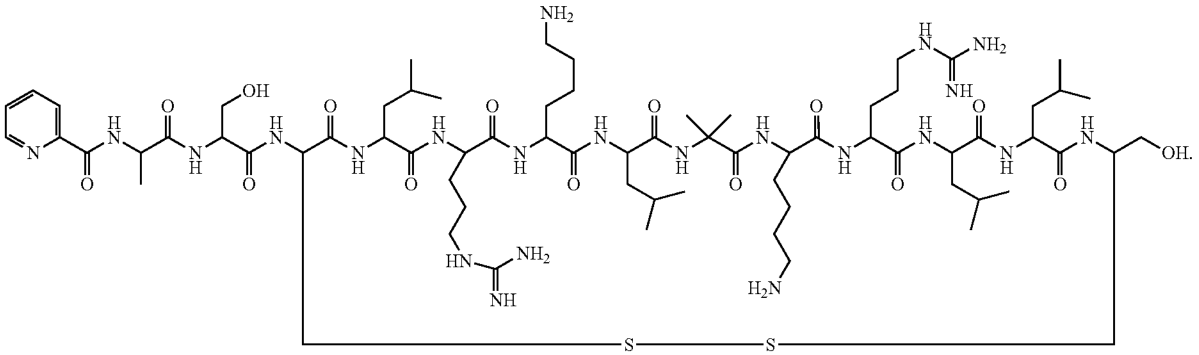

The method of forming a peptide alcohol compound having —OH at the amino acid terminal is known to those skilled in the art, and for example, see Neugebauer, W., Escher, E. Helve. Chim. Acta. 72: 1318-1323. (1989); Liu, etc., Chinese Journal of Medicinal Chemistry. 14 (1): 33-35 (2004); Chaturvedi, N C, et al, U.S. Pat. No. 6,987,167 (2006); Wu, Y.-T., et al, J. Chinese Chem. Soc. 46 (2): 135-138 (2013).

For example, a modification of Compound 2 may also be a cyclic peptide compound with the following peptide aldehyde structure that is named as Compound 3:

(SEQ ID NO: 20, Compound 3)

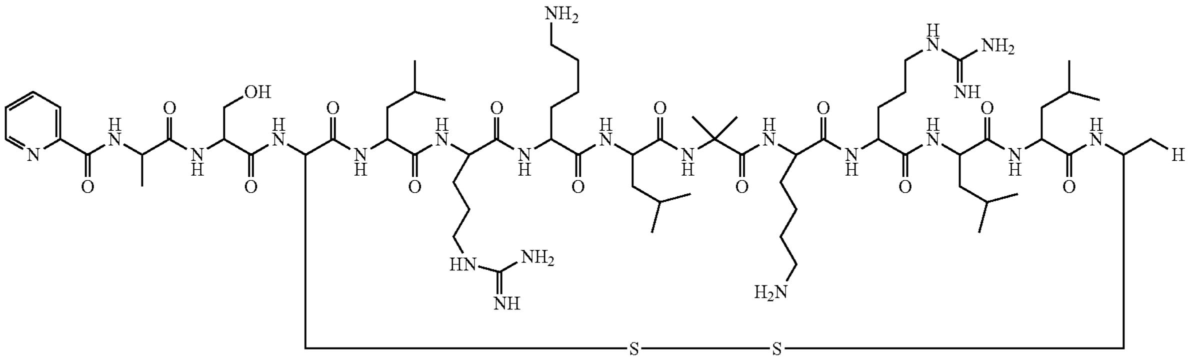

Methods of forming peptide aldehyde compounds, such as those embodiments of the present invention in which the terminal amino acid has a —C(O)H, are known to those of skill, see, for example, see Fehrentz, J A, et Al, Tetrahedron Lett. 36: 7871-7874 (1995); Douat, C., et al, Tetrahedron Lett. 41 (1): 37-49. (2000); Moulin, A., et al, J. Peptide Sci. 13 (1): 1-15 (2010).

In some aspects of the present invention, the cyclic peptide compounds are formed between the side-chain of two of the internal amino acids X3, X8, and X13 by a chemical bond selected from the group of: —SS—, —$CH_2$—S—$CH_2$—, —CO—NH—, —CO—O—, —$CH_2$—NH—, —$CH_2$—$CH_2$—, —S—$(CH_2)$n-$R_1$—$(CH_2)$n-S— ($R_1$ is hydrocarbon, aryl or heteroaryl, n=1-3), —CO—$CH_2$—S—$CH_2$— or —CO—NH— chemical bonds. Construction of a chemical bond is formed between two amino acid residue side chains to form a cyclic peptide using methods known to the skilled person.

For example, the way of forming —SS— between amino acids within the cyclic peptide compound of the present invention is known to those skilled in the art, and can be found in, for example, Pohl, M., et al, J. Peptide Protein Res. 41 (4): 362-375. (1993); Tam, J P, et al, J ACS. 113 (17): 6657-6662. (1991); and in Example I of the present disclosure, which describes a method of preparation of the cyclic peptide compounds.

As another example, the manner of forming —$CH_2$—S—$CH_2$— between the side-chains of the amino acids within the cyclic peptide compound of the present invention is also known to those skilled in the art, and can be seen, for example, in Aimetti, A A, et al, Chem. Commun. 46: 4061-4063. (2010); Elduque, X., et al, J. Org. Chem. 79 (7): 2843-2853 (2014).

For example, Compound 4 and Compound 5 can be the following cyclic peptide compound having a stable cyclic peptide bond:

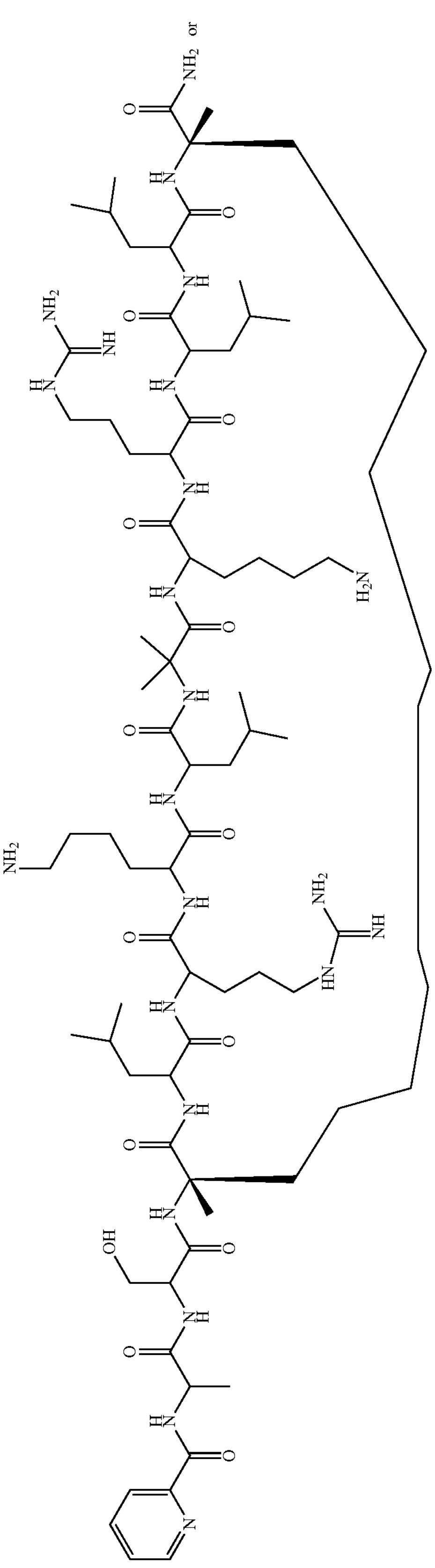
(SEQ ID NO: 22, Compound 4)
or
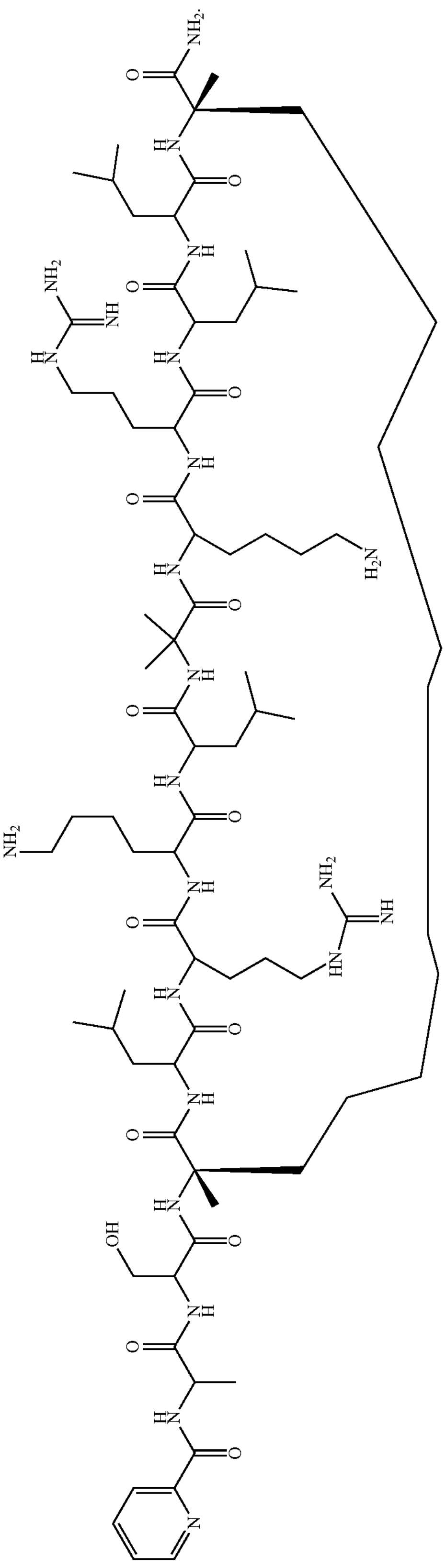
(SEQ ID NO: 22, Compound 5)

In the stabilized forms of the cyclic peptide compounds shown above, the cyclic peptide bond is formed by $-(CH_2)n-$ (n=2-15) or $-(CH_2)n-CH{=}CH-(CH_2)n-$ (n=2-15). The method of forming these stable bonds may be found, for example, in Chang, Y S, et al, PNAS. 110 (36): E3445-E3454. (2013); Kim, Y.-W., et al, Nature Protocols. 6 (6): 761-771 (2011); Spiegel, J., et al, Angew. Chem. Int. Ed. 53 (9): 2498-2503. (2014).

(iv) Medical Use of the Cyclic Peptide Compound of the Present Invention

In one aspect, the present invention provides the use of a cyclic peptide compound in the preparation of a pharmaceutical composition for the prevention and/or treatment of stroke, related conditions, and/or inflammatory diseases. In one aspect, the cyclic peptide compound of the present invention can be used to prevent and/or treat stroke, related conditions, and/or inflammatory diseases.

Experiments have confirmed that embodiments of the cyclic peptide compound of the present invention can have a stable structure, low biological toxicity, and excellent therapeutic and/or preventive effects on stroke and/or related diseases (see Examples I and II).

The term "stroke" is an acute cerebrovascular disease, where brain blood vessels, due to sudden rupture due to vascular occlusion or a group of diseases caused by brain tissue damage, including "ischemic cerebral stroke" and "hemorrhagic cerebral stroke" has occurred.

"Ischemic stroke" can also be called "cerebral infarction", "ischemic stroke" or "ischemia". Unless otherwise stated, "cerebral infarction", "ischemic stroke", and "ischemia" are used interchangeably herein.

"Hemorrhagic brain stroke" may also be referred to as a "brain hemorrhage" and "hemorrhagic stroke". Unless otherwise noted, "hemorrhagic brain stroke", "brain hemorrhage", "intracranial hemorrhage", "hemorrhagic stroke" are used interchangeably herein.

"Neurodegenerative diseases" are caused by the loss of neurons and/or their myelin sheaths, which deteriorate over time and appear dysfunctional. "Neurodegenerative diseases" include but are not limited to Alzheimer's disease (AD), Parkinson's disease (PD), Huntington's disease (HD), amyotrophic lateral sclerosis (ALS), different types of spinocerebellar ataxia (SCA), Pick's disease, Frontotemporal Dementia (FTD or FTDP-17), etc.

The term "treatment" as used herein means administration of the medicament of the present invention to an individual suffering from a disease or disease condition that results in partial or complete remission of the symptoms, or prevents aggravation of the symptoms of the disease and/or disease condition after treatment. Therefore, treatment includes cure. As used herein, "efficacy" represents the effect caused by the treatment, which changes, generally changes, alleviates or ameliorates symptoms or characteristics of a disease or condition, or that cures a disease or condition. "Treatment" may also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment and is not necessarily meant to imply complete cessation of the condition.

The term "prevention" as used herein means that before perceptible symptoms appear or occur in a disease or condition that administration of drug or medication is designed to treat or to prevent the underlying disease occurrence and/or development. Unless otherwise stated, the terms of the present invention include "treatment", and in certain conditions and/or diseases, may also include prophylactic administration.

As used herein, the term "therapeutically effective amount" refers to the use of or the method of delivery of an amount of active ingredient that will achieve the desired therapeutic efficacy after being administered.

In some embodiments of the uses or methods described herein, the dose of the cyclic peptide compound of the present invention generally depends on a variety of factors, including the severity of the individual or combined disorder or condition or disease being treated, the rate of administration, and the judgment of the prescribing physician. In general, the effective daily dose per kg body weight can range from about 0.01 to about 1.0 mg, for example, about 0.01 to about 1.0, 0.01 to about 0.1, 0.01 to about 0.09, 0.01 to about 0.08, 0.01 to about 0.07, 0.01 to about 0.06, 0.01 to about 0.05, or 0.01 to about 0.04 mg/kg/day. In one embodiment, the dose is 0.051 mg/kg/day on the first day followed by 0.017 mg/kg/day on subsequent days. The precise dose may be varied on each day of dosing to achieve the desired therapeutic efficacy.

In some embodiments of the uses or methods described herein, the cyclic peptide compound of the present invention can be administered in a single administration or in multiple administrations. In one embodiment, multiple administrations include: once a day, twice a day, three times a day, once a week, twice a week, three times a week, four times a week, once every two weeks, or once a month.

As used herein, the term "subject" includes a human patient and a non-human (animal) patient. The term "non-human animal" includes vertebrates, for example, mammals, such as non-human primates, sheep, cows, dogs, cats, and rodents such as mice and rats.

(v) The Pharmaceutical Composition of the Cyclic Peptide Compound of the Present Invention In one aspect, the present invention also provides a pharmaceutical composition comprising the cyclic peptide compound of the present invention as an active ingredient. The composition of the present invention may further include pharmaceutically acceptable excipients. A person skilled in the art can select an appropriate excipient according to the desired formulation form, administration mode, and drug release characteristics of the drug. For example, embodiments of the present invention include pharmaceutically acceptable excipients including one or more of: excipients, disintegrants, diluents, binders, solvents, co-solvents, lubricants, pH adjusting agents, buffers, preservatives, dispersants, suspending agents, ointment bases, emulsifiers, emollients, penetration enhancers, surfactants, propellants, flavoring agents, sweeteners, and/or drug release modifiers.

In one embodiment of the pharmaceutical composition comprising the cyclic peptide compound of the present invention, the pharmaceutically acceptable excipients include excipients, pH adjusting agents, buffers, solvents and/or binders.

In one embodiment, the excipient comprises mannitol.

In one embodiment, the pH adjusting agent includes one or more of hydrochloric acid, acetic acid, tartaric acid, citric acid, and/or sodium hydroxide.

In one embodiment, the buffering agent includes one or more of an alkali metal salt solution of citric acid and an alkali metal salt solution of phosphoric acid, preferably sodium citrate salt solution and/or sodium phosphate salt solution.

In one embodiment, the solvent includes one or more of physiological saline and/or glucose solution.

In one embodiment, the binder comprises sodium carboxymethyl cellulose.

In one embodiment, the active agent of the present invention and its compositions may be formulated for administration in any solid, semi-solid, or liquid dosage forms that are acceptable modes of administration available in the art, including, but not limited to: (1) suitable for oral administration: such as tablets, capsules, powders, granules, lozenges, aqueous or non-aqueous solutions or suspensions, syrups, etc.; (2) suitable for parenteral administration: such as subcutaneous, intramuscular or intravenous injection, such as sterile solutions or suspensions; (3) suitable for local administration: for example, plaster, ointment, cream, spray or gel for skin or mucous membrane; (4) suitable for transdermal administration: for example, patches, gel ointments, etc.; (5) suitable for vaginal or rectal administration: for example, suppositories, emulsions, gels, or effervescent tablets.

In one embodiment, the active agent of the pharmaceutical composition of the present invention may be selected from one or more dosage forms: freeze-dried powder injection, water injection, slow release agents, and/or sprays.

The present invention will be described in more detail below through examples, but these examples do not limit the present invention in any way.

EXAMPLES

Example I. Preparation of Cyclic Peptide Compounds (1). Preparation and Characterization of Compound 1

The solid phase reaction column was 0.328 mmol/g of Fmoc-Rink amide MBHA resin (3.1 g) and was washed twice with DMF (N,N-dimethylformamide), followed by swelling in DMF for 30 min in a cylindrical reaction vessel. The Fmoc protecting groups were deprotected by treating twice with 20% piperidine/DMF. After thoroughly washing 6 times with DMF, the resin was tested with ninhydrin reagents. The deep blue color of the resin indicated that the Fmoc groups had been removed.

2.34 g Fmoc-Cys(Trt)-OH (4.0 mmol), 540 mg HOBt (4.0 mmol), and 1500 mg HBTU (4.0 mmol) were weighed and dissolved in DMF in a reaction vessel, followed by the addition of 1 ml DIPEA (6.0 mmol). The reaction mixture was allowed to react at room temperature for 1.5 h, with ninhydrin test to determine the completion of the reaction. If the resin is colorless and transparent, the reaction was completed; if the resin was colored, the reaction was not complete and the coupling was extended by another hour (1 h more). This criterion applies to subsequent ninhydrin tests to determine endpoint of the reaction. The resin was washed four times with DMF, and then the synthetic cycles for each amino acid were repeated by removing the Fmoc protection group and coupling the next corresponding amino acid until completion of all subsequent amino acids in the proper order according to the amino-acid-sequence of the peptide main chain were completed. After removing the final Fmoc protecting group at the N-termini (amino terminus of peptide), the peptide-bound resin was washed 6 times with DMF. To the reaction vessel, a mixture of 500 mg of picolinic acid (4.0 mmol), 540 mg of HOBt (4.0 mmol), and 1500 mg of HBTU (4.0 mmol) in DMF was added, followed by the addition of 1 ml DIPEA (6.0 mmol). The reaction was incubated at room temperature for 1.5 h, with ninhydrin test to determine the completion of the reaction. If the color is transparent, the reaction is complete, otherwise, the reaction was continued or repeated. Finally, the peptide-bound resin was washed twice with DMF, then twice with methanol, twice with methyl tert-butyl ether (MTBE), and dried in vacuo to give 6.3 g of peptide resin.

6.3 g of Compound 1 peptide-bound resin was weighed and added to a 100 ml round-bottom flask containing 41 ml of TFA cleavage cocktail (TFA:TIS:$H_2O$:DTT at 95:2.5:2.5:7.0 v/v/v/w). The cleavage reaction was carried out at room temperature with stirring for 2 hours. After the reaction was completed, the resin was filtered, the filtrate was collected, and the resin was washed with a small amount of TFA. The crude peptide was precipitated by addition of 650 ml of pre-cooled anhydrous MTBE and centrifuged, the peptide pellet washed with MTBE four times, and dried in vacuo to give 1900 mg of crude Compound 1 (crude yield 119.4%. ESI-MS: 1592.66 (Calculated M.W.: 1593.05).

1900 mg (about 1 mmol) of linear Compound 1 peptide was weighed and added to a 2 L volumetric flask containing 1 L of acetic acid aqueous solution (HOAc:$H_2O$=5:95, v/v), and dissolved completely. To this peptide solution, an iodine solution in methanol was added dropwise while stirring. After the acetic acid aqueous solution containing Compound 1 changed color, more iodine solution was added as appropriate. The reaction was then placed on a stirrer for 1 h, a sample collected, and the mass was detected by ESI-MS: 1590.58 (Calculated M.W.: 1591.04 for cyclized peptide), and a sufficient amount of vitamin C aqueous solution was added to terminate the reaction (the color of the Compound 1 acetic acid aqueous solution faded). The reaction mixture was freeze-dried.

2000 mg of crude Compound 1 cyclic peptide was weighed, dissolved in 10 mL of a mixed solvent of 2 ml of acetonitrile+8 ml of water (1:4, v/v), and purified by RP-HPLC (Waters Prep150 system with an ultraviolet (UV) detector set to a wavelength of 214 nm) on a 30×250 mm reverse-phase C18 semi-preparative column at room temperature. The peptide on the column was eluted using a conventional gradient from 0.1% TFA/$H_2O$ to 0.1% TFA/acetonitrile of mobile phase to elute the peak UV-absorbing fraction that was collected and found to contain 98.0% pure peptide. The peptide was concentrated by rotary evaporation, freeze dried to give Compound 1 trifluoroacetate fine cyclic peptide 575.0 mg of pure cyclic Compound 1 peptide trifluoroacetate with an HPLC purity of 98.5% (purification yield 28.8%), and ESI-MS: 1590.58 (Calculated M.W.: 1591.04). The total yield was 19.2%.

Exchanging salt form of the peptide: 575.0 mg of cyclic Compound 1 peptide trifluoroacetate was weighed and dissolved in 6.4 ml of a solution containing 0.4 ml acetonitrile+6.0 ml of water, and loaded onto a 30×250 mm reverse phase C18 column at room temperature. Peptide was purified in a conventional gradient from 100% of 0.1% HOAc/$H_2O$ to 100% of 0.1% HOAc/acetonitrile. The peak fractions were collected, concentrated by rotary evaporation, and freeze-dried to give 350.0 mg of cyclic Compound 1 peptide acetate. HPLC purity was 97.88% (purification yield 60.9%) and ESI-MS: 1590.58 (Calculated M.W.: 1591.04). The total yield was 11.7%.

Example II. The Biological Activity Test on Cyclopeptide Compounds (1) Biological Activity of Cyclic Peptide Compounds In Vitro In Vitro TNF-α Inhibitory Activity of Compound 1

To measure the efficacy of the biological activity of Compound 1, an in vitro assay was employed to measure TNF-α content in conditioned media of cells treated with lipopolysaccharide (LPS) and different concentrations of Compound 1. 1 mg of Compound 1 peptide compound was added to 3.333 mL of physiological saline to make a 189 μM peptide solution which is sterilized by filtration through a 0.22 μm membrane filter. For treatment of cells, threefold serial dilutions were made, yielding concentrations of 189, 63, 21, 7, 2.3, and 0.76 μM peptide solution.

BV2 cells were recovered and passaged more than 3 times. $1.2\times10^6$ BV2 microglial cells in good growth state and in the logarithmic growth phase were diluted to 1.25×10 cells/mL with DMEM medium containing 10% FBS, and 400 μL of cell suspension was inoculated into each well of a 48-well cell culture plate. After 6 hr incubation in a $CO_2$ incubator, the supernatant was aspirated, and replaced with 400 μL DMEM medium (1% FBS+1% Penicillin/Streptomycin) and 20 μL of each concentration of Compound 1 was added to each well, placed in a $CO_2$ incubator for 45 min, and then 20 μL LPS (concentration of LPS solution is 22 μg/mL LPS (Sigma-L6529) was added to each well, with a set of 3 or more wells for each cyclic peptide compound concentration. After incubation for 24 h at 37° C. in a $CO_2$ incubator (5% of $CO_2$), 100 μL of supernatant from each well was placed into single wells of a 96 well plate and centrifuged at 1000 rpm for 5 min. After centrifugation, 10 μL of supernatant from each well was used for TNF-α content detection (TNF-α detection kit, Unitech Biochemical Catalog No.: 70-EK282/3-96). $IC_{50}$ calculations using TNF-α content was performed with GraphPad Prism software to find that Compound 1 gave an $IC_{50}$ of about 1.02 μM for reducing LPS-induced TNF-α content by half, which is one measure of efficacy and/or potency.

(2) Biological Activity of Cyclic Peptide Compounds In Vivo

In Vivo TNF-α Inhibitory Activity of Compound 1

To measure the efficacy of the biological activity of Compound 1, an in vivo assay was employed to measure TNF-α content in the blood of whole mice treated with lipopolysaccharide (LPS) and different concentrations of Compound 1. 56 ICR male mice, 12-14 g, were acclimated to the animal facility for 7 days and were then randomized into 8 groups with 7 mice/group to receive doses of 0, 0.001, 0.003, 0.01, 0.03, 0.1, 0.3, and 1.0 mg/kg of compound. Each dose group received intravenous (IV) injection of different concentrations of Compound 1 peptide solution at a dosing volume of 10 mL/kg. 30 min later, IV LPS at a dose of 5 μg/kg and at a volume of 10 ml/kg was administered. 1.5 hours after administration of LPS, whole blood was collected from the orbit of ICR mice, centrifuged at 4000 rpm for 10 min, and the supernatant was collected and used for TNF-α content detection from each of the different Compound 1 doses. (TNF-α detection kit, Unitech biological item number: 70-EK282/3-96). The $ED_{50}$ (Effective Dose at which a 50% reduction in blood TNF-α content was found) for Compound 1 was calculated to be 0.045 mg/kg using Graphpad Prism software.

The invention claimed is:

1. A cyclic peptide compound having the general formula (I):

(SEQ ID NO: 1)

(I)

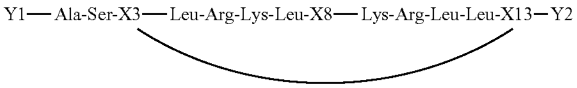

wherein:

X3 is Cys, Glu, Asp, Lys, Orn, 2,4-Diaminobutyric Acid (Dab), 2,3-Diaminopropionic Acid (Dap), Ser, Gln, or halogenated alanine, or their corresponding enantiomeric D-amino acids;

X13 is Cys, Glu, Asp, Lys, Orn, Dab, Dap, Ser, Gln, or halogenated alanine, or their corresponding enantiomeric D-amino acids;

X8 is Aib;

The symbol "⌣" represents a chemical bond between X3 and X13, wherein the chemical bond is selected from:

—SS—, —$CH_2$—S—$CH_2$—, —CO—NH—, —CO—O—, —$CH_2$—NH—, —$(CH_2)n$ (n=2-15), or —$(CH_2)n$-CH═CH—$(CH_2)n$ (n=2-15); or

—S—$(CH_2)n$-$R_1$—$(CH_2)n$-S—, wherein $R_1$ is a hydrocarbon group, an aryl group or a heteroaryl group, n=1-3;

Y1 is present or absent, and when present, Y1 is $R_2$—CO—, wherein $R_2$ is a hydrocarbon group, an aryl group, or a heteroaryl group;

Y2 is present or absent, and when present, Y2 is a carboxy-terminal group.

2. The cyclic peptide compound of claim 1, wherein:

X13 is Cys, X8 is Aib, and X3 is Cys (SEQ ID NO: 2);

X13 is Cys, X8 is Aib, and X3 is D-Cys (SEQ ID NO: 3);

X13 is D-Cys, X8 is Aib, and X3 is Cys (SEQ ID NO: 4);

X13 is D-Cys, X8 is Aib, and X3 is D-Cys (SEQ ID NO: 5);

X13 is a Glu or Asp, X8 is Aib, and X3 is a Lys, Orn, Dab, or Dap (SEQ ID NO: 6);

X13 is a Lys, Orn, Dab, or Dap, X8 is Aib, and X3 is a Glu or Asp (SEQ ID NO: 7);

X13 is a Glu or Asp, X8 is Aib, and X3 is a D-Lys, D-Orn, D-Dab, or D-Dap (SEQ ID NO: 8);

X13 is a D-Glu or D-Asp, X8 is Aib, and X3 is a Lys, Orn, Dab, or Dap (SEQ ID NO: 9);

X13 is a D-Glu or D-Asp, X8 is Aib, and X3 is a D-Lys, D-Orn, D-Dab, or D-Dap (SEQ ID NO: 10);

X13 is a Lys, Orn, Dab, or Dap, X8 is Aib, and X3 is a D-Glu or D-Asp (SEQ ID NO: 11);

X13 is a D-Lys, D-Orn, D-Dab, or D-Dap, X8 is Aib, and X3 is a Glu or Asp (SEQ ID NO: 12);

X13 is a D-Lys, D-Orn, D-Dab, or D-Dap, X8 is Aib, and X3 is a D-Glu or D-Asp (SEQ ID NO: 13);

X13 is halogenated alanine, X8 is Aib, and X3 is Cys (SEQ ID NO: 14);

X13 is halogenated D-alanine, X8 is Aib, and X3 is Cys (SEQ ID NO: 15); or

X13 is halogenated D-alanine, X8 is Aib, and X3 is D-Cys (SEQ ID NO: 16).

3. The cyclic peptide compound of claim 1, wherein:

Y1 is $R_2$CO—, and wherein $R_2$ is: C1-C4 linear or branched alkyl, C2-C4 linear or branched alkenyl, C2-C4 alkynyl, a 5-10 membered aryl, or a 5-10 membered heteroaryl O, S, or N.

4. The cyclic peptide compound of claim 1, wherein:

Y1 is acetyl, picolinoyl or pyrazinecarbonyl.

5. The cyclic peptide compound of claim 1, wherein the —COOH ends of the amino acids represented by Y2 and X13 form a structure —$CH_2$OH or —COR, wherein R is —$NH_2$, H, —$CH_3$, —$OCH_3$, —$OC_2H_5$, —$CH_3$, —NH—OH, —NH—$CH_3$, —$N(CH_3)_2$, —NH—$C_2H_5$, —NH—$C_6H_5$, or —NH—$C_6H_4$—$NO_2$.

6. The cyclic peptide compound of claim 1, wherein: $R_2$ is phenyl or cyclopropyl.

7. The cyclic peptide compound of claim 1, wherein the cyclic peptide compound is:

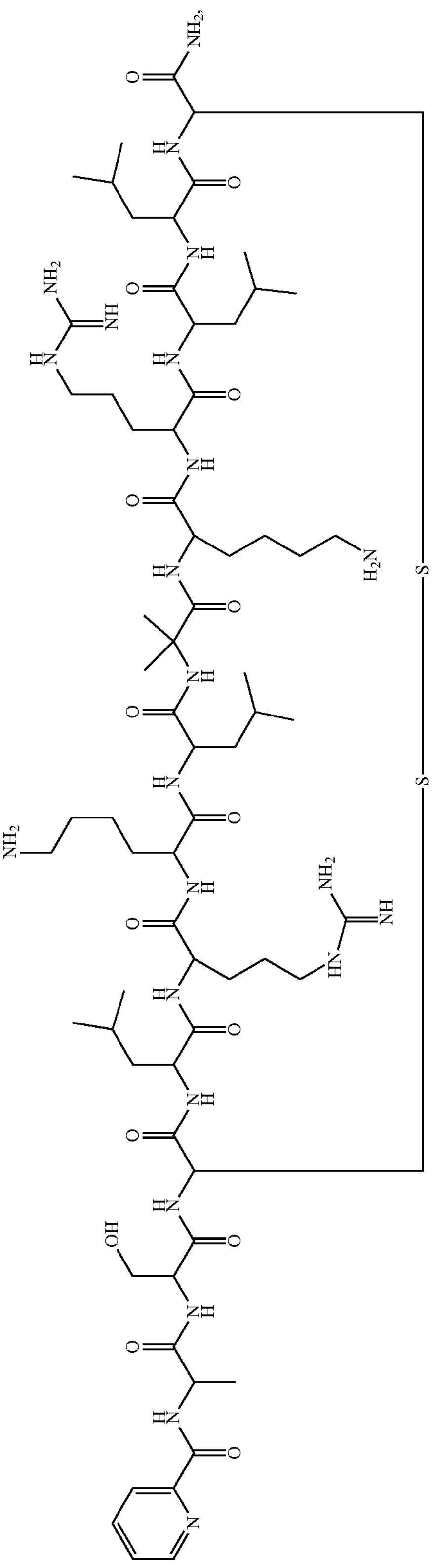
(SEQ ID NO: 18, Compound 1)
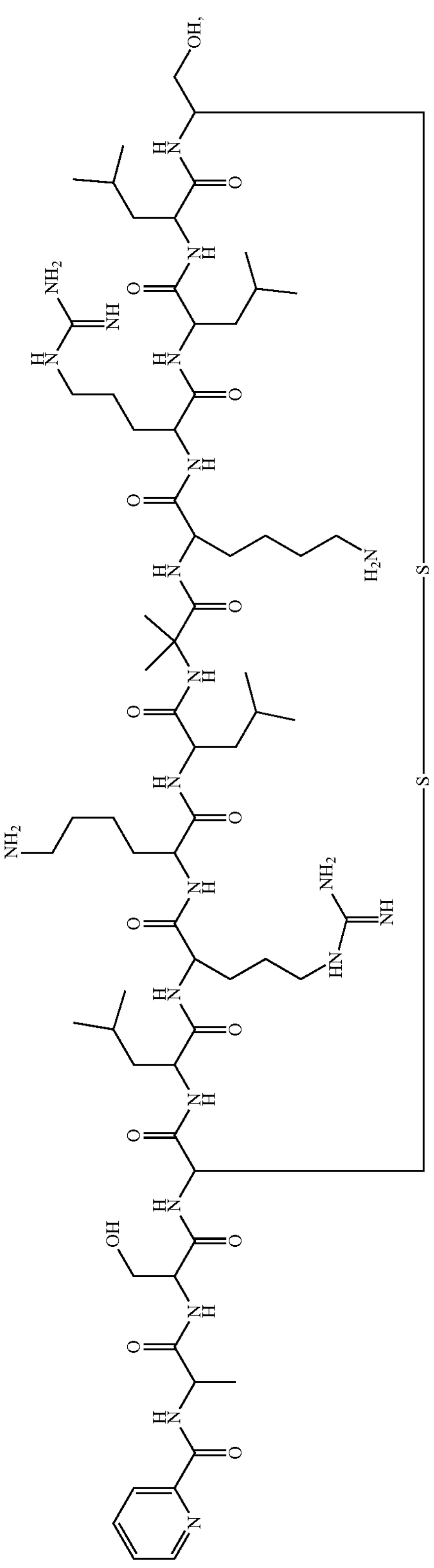
(SEQ ID NO: 19, Compound 2)

-continued
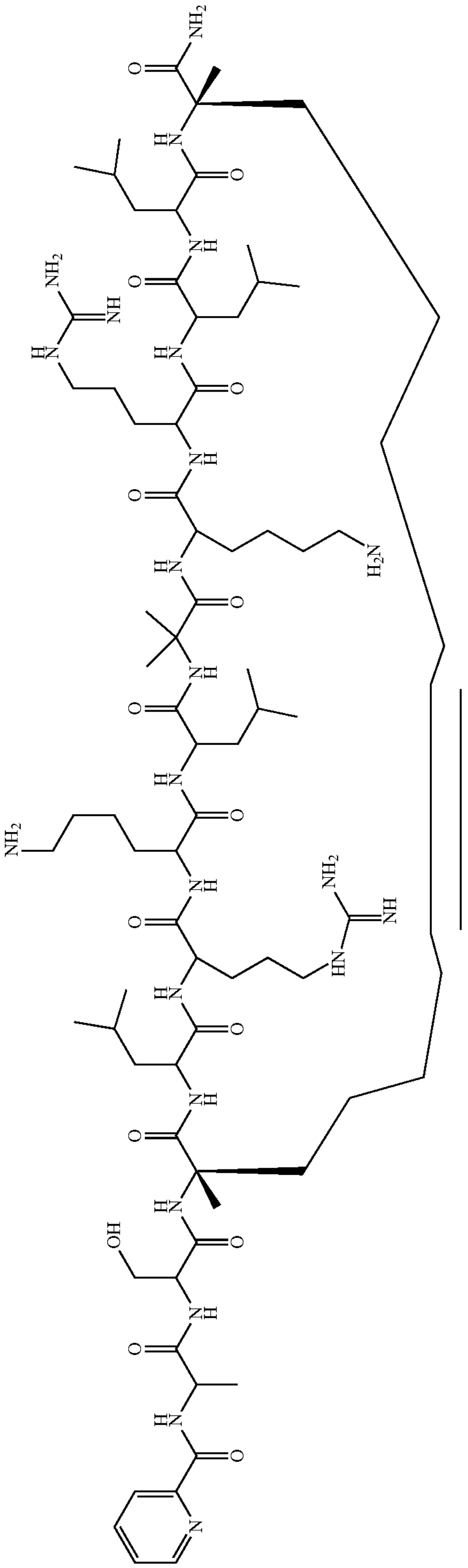
(SEQ ID NO: 22, Compound 4)
or
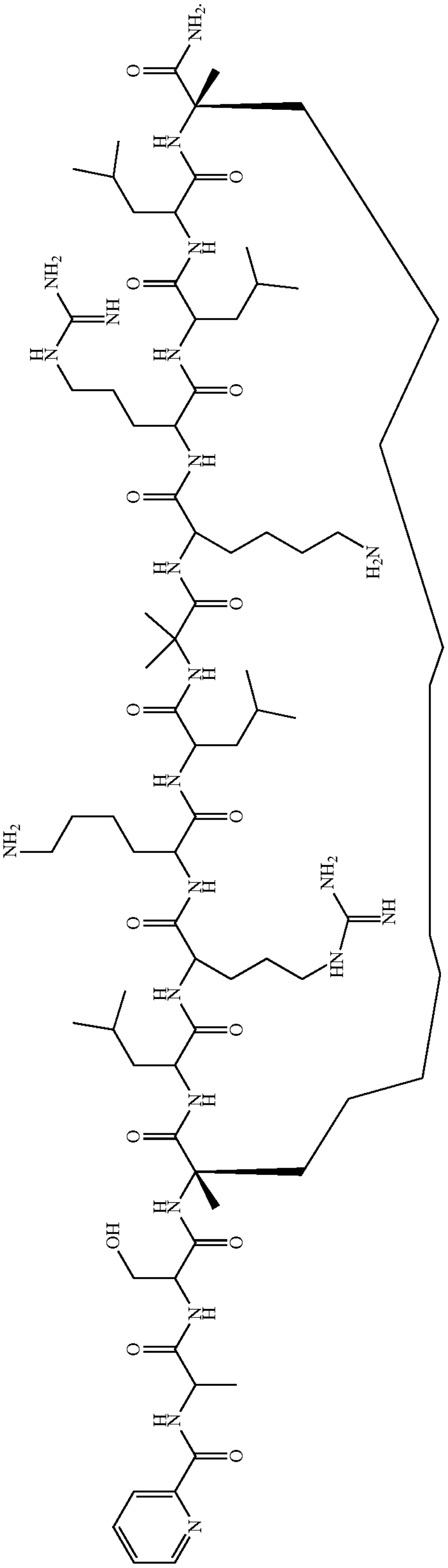
(SEQ ID NO: 22, Compound 5)

8. A pharmaceutical composition comprising the cycle peptide compound of claim 1, or a pharmaceutically acceptable salt or solvate thereof.

9. The pharmaceutical composition of claim 8, further comprising a pharmaceutically acceptable excipient.

10. The pharmaceutical composition of claim 9, wherein said pharmaceutically acceptable excipient comprises one or more of: excipients, disintegrants, diluents, binders, solvents, co-solvents, lubricants, the pH adjusting agents, buffering agents, preservatives, dispersing agents, suspending agents, ointment bases, emulsifiers, emollients, penetration agents, surfactants, propellants, flavoring agents, sweetening agents, or drug release modifiers.

* * * * *

SEQUENCE LISTING

```
Sequence total quantity: 22
SEQ ID NO: 1            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
VARIANT                 3
                        note = MISC_FEATURE - Cys, Glu, Asp, Lys, Ornithine,
                         2,4-Diaminobutyric Acid (Dab), 2,3-Diaminopropionic Acid
                         (Dap), Ser, Gln, halogenated alanine, or their
                         corresponding enantiomeric D-amino acids
SITE                    8
                        note = MISC_FEATURE - amino iso-butyric acid (Aib)
VARIANT                 13
                        note = MISC_FEATURE - Cys, Glu, Asp, Lys, Ornithine,
                         2,4-Diaminobutyric Acid (Dab), 2,3-Diaminopropionic Acid
                         (Dap), Ser, Gln, halogenated alanine, or their
                         corresponding enantiomeric D-amino acids, which may be
                         modified with a carboxy-terminal group
CROSSLNK                3..13
                        note = MISC_FEATURE - Chemical bond between residues 3 and
                         13 is selected from SS-, -CH2-S-CH2 -, -CO-NH-, -CO-O-,
                         -CH2-NH-, -(CH2)n- (n = 2-15), -(CH2)n-CH=CH-(CH2)n- (n =
                         2-15), or -S-(CH2)n -R1-(CH2)n -S-, wherein R1 is a
                         hydrocarbon group, an aryl group or a heteroaryl group, n
                         = 1-3
SEQUENCE: 1
ASXLRKLXKR LLX                                                          13

SEQ ID NO: 2            moltype = AA  length = 13
FEATURE                 Location/Qualifiers
```

-continued

```
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
SITE                    8
                        note = MISC_FEATURE - amino iso-butyric acid (Aib)
VARIANT                 13
                        note = Cys, which may be modified with a carboxy-terminal
                         group
DISULFID                3..13
                        note = MISC_FEATURE - There is a disulfide chemical bond
                         between residue 3 and 13
SEQUENCE: 2
ASCLRKLXKR LLC                                                      13

SEQ ID NO: 3            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
SITE                    3
                        note = MISC_FEATURE - D-Cys
SITE                    8
                        note = MISC_FEATURE - amino iso-butyric acid (Aib)
VARIANT                 13
                        note = Cys, which may be modified with a carboxy-terminal
                         group
SITE                    3..13
                        note = MISC_FEATURE - There is a chemical bond between the
                         side chains of residue 3 and 13
SEQUENCE: 3
ASCLRKLXKR LLC                                                      13

SEQ ID NO: 4            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
SITE                    8
                        note = MISC_FEATURE - amino iso-butyric acid (Aib)
VARIANT                 13
                        note = MISC_FEATURE - D-Cys, which may be modified with a
                         carboxy-terminal group
SITE                    3..13
                        note = MISC_FEATURE - There is a chemical bond between the
                         side chains of residue 3 and 13
SEQUENCE: 4
ASCLRKLXKR LLC                                                      13

SEQ ID NO: 5            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
SITE                    3
                        note = MISC_FEATURE - D-Cys
SITE                    8
                        note = MISC_FEATURE - amino iso-butyric acid (Aib)
VARIANT                 13
                        note = MISC_FEATURE - D-Cys, which may be modified with a
                         carboxy-terminal group
SITE                    3..13
                        note = MISC_FEATURE - There is a chemical bond between the
                         side chains of residue 3 and 13
```

-continued

```
SEQUENCE: 5
ASCLRKLXKR LLC                                                   13

SEQ ID NO: 6            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
VARIANT                 3
                        note = MISC_FEATURE - Lys, Orn, 2,4-Diaminobutyric Acid
                         (Dab), or 2,3-Diaminopropionic Acid (Dap)
SITE                    8
                        note = MISC_FEATURE - amino iso-butyric acid (Aib)
VARIANT                 13
                        note = MISC_FEATURE - Glu or Asp, which may be modified
                         with a carboxy-terminal group
SITE                    3..13
                        note = MISC_FEATURE - There is a chemical bond between the
                         side chains of residue 3 and 13
SEQUENCE: 6
ASXLRKLXKR LLX                                                   13

SEQ ID NO: 7            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
VARIANT                 3
                        note = MISC_FEATURE - Glu or Asp
SITE                    8
                        note = MISC_FEATURE - amino iso-butyric acid (Aib)
VARIANT                 13
                        note = MISC_FEATURE - Lys, Orn, 2,4-Diaminobutyric Acid
                         (Dab), or 2,3-Diaminopropionic Acid (Dap), which may be
                         modified with a carboxy-terminal group
SITE                    3..13
                        note = MISC_FEATURE - There is a chemical bond between the
                         side chains of residue 3 and 13
SEQUENCE: 7
ASXLRKLXKR LLX                                                   13

SEQ ID NO: 8            moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
VARIANT                 3
                        note = MISC_FEATURE - D-Lys, D-Ornithine,
                         D-2,4-Diaminobutyric Acid (D-Dab), or
                         D-2,3-Diaminopropionic Acid (D-Dap)
SITE                    8
                        note = MISC_FEATURE - amino iso-butyric acid (Aib)
VARIANT                 13
                        note = MISC_FEATURE - Glu or Asp, which may be modified
                         with a carboxy-terminal group
SITE                    3..13
                        note = MISC_FEATURE - There is a chemical bond between the
                         side chains of residue 3 and 13
SEQUENCE: 8
ASXLRKLXKR LLX                                                   13

SEQ ID NO: 9            moltype = AA  length = 13
FEATURE                 Location/Qualifiers
source                  1..13
                        mol_type = protein
                        organism = synthetic construct
VARIANT                 1
```

-continued

```
                     note = Alanine attached to a hydrocarbon group, an aryl
                      group, or a heteroaryl group via a carbonyl group, or
                      attached to nothing
VARIANT              3
                     note = MISC_FEATURE - Lys, Orn, 2,4-Diaminobutyric Acid
                      (Dab), or 2,3-Diaminopropionic Acid (Dap)
SITE                 8
                     note = MISC_FEATURE - amino iso-butyric acid (Aib)
VARIANT              13
                     note = MISC_FEATURE - D-Glu or D-Asp, which may be modified
                      with a carboxy-terminal group
SITE                 3..13
                     note = MISC_FEATURE - There is a chemical bond between the
                      side chains of residue 3 and 13
SEQUENCE: 9
ASXLRKLXKR LLX                                                    13

SEQ ID NO: 10        moltype = AA  length = 13
FEATURE              Location/Qualifiers
source               1..13
                     mol_type = protein
                     organism = synthetic construct
VARIANT              1
                     note = Alanine attached to a hydrocarbon group, an aryl
                      group, or a heteroaryl group via a carbonyl group, or
                      attached to nothing
VARIANT              3
                     note = MISC_FEATURE - D-Lys, D-Ornithine,
                      D-2,4-Diaminobutyric Acid (D-Dab), or
                      D-2,3-Diaminopropionic Acid (D-Dap)
SITE                 8
                     note = MISC_FEATURE - amino iso-butyric acid (Aib)
VARIANT              13
                     note = MISC_FEATURE - D-Glu or D-Asp, which may be modified
                      with a carboxy-terminal group
SITE                 3..13
                     note = MISC_FEATURE - There is a chemical bond between the
                      side chains of residue 3 and 13
SEQUENCE: 10
ASXLRKLXKR LLX                                                    13

SEQ ID NO: 11        moltype = AA  length = 13
FEATURE              Location/Qualifiers
source               1..13
                     mol_type = protein
                     organism = synthetic construct
VARIANT              1
                     note = Alanine attached to a hydrocarbon group, an aryl
                      group, or a heteroaryl group via a carbonyl group, or
                      attached to nothing
VARIANT              3
                     note = MISC_FEATURE - D-Glu or D-Asp
SITE                 8
                     note = MISC_FEATURE - amino iso-butyric acid (Aib)
VARIANT              13
                     note = MISC_FEATURE - Lys, Ornithine, 2,4-Diaminobutyric
                      Acid (Dab), or 2,3-Diaminopropionic Acid (Dap), which may
                      be modified with a carboxy-terminal group
SITE                 3..13
                     note = MISC_FEATURE - There is a chemical bond between the
                      side chains of residue 3 and 13
SEQUENCE: 11
ASXLRKLXKR LLX                                                    13

SEQ ID NO: 12        moltype = AA  length = 13
FEATURE              Location/Qualifiers
source               1..13
                     mol_type = protein
                     organism = synthetic construct
VARIANT              1
                     note = Alanine attached to a hydrocarbon group, an aryl
                      group, or a heteroaryl group via a carbonyl group, or
                      attached to nothing
VARIANT              3
                     note = MISC_FEATURE - Glu or Asp
SITE                 8
                     note = MISC_FEATURE - amino iso-butyric acid (Aib)
VARIANT              13
                     note = MISC_FEATURE - D-Lys, D-Ornithine,
```

-continued

```
                      D-2,4-Diaminobutyric Acid (D-Dab), or
                      D-2,3-Diaminopropionic Acid (D-Dap), which may be modified
                      with a carboxy-terminal group
SITE                  3..13
                      note = MISC_FEATURE - There is a chemical bond between the
                      side chains of residue 3 and 13
SEQUENCE: 12
ASXLRKLXKR LLX                                                        13

SEQ ID NO: 13         moltype = AA  length = 13
FEATURE               Location/Qualifiers
source                1..13
                      mol_type = protein
                      organism = synthetic construct
VARIANT               1
                      note = Alanine attached to a hydrocarbon group, an aryl
                      group, or a heteroaryl group via a carbonyl group, or
                      attached to nothing
VARIANT               3
                      note = MISC_FEATURE - D-Glu or D-Asp
SITE                  8
                      note = MISC_FEATURE - amino iso-butyric acid (Aib)
VARIANT               13
                      note = MISC_FEATURE - D-Lys, D-Ornithine,
                      D-2,4-Diaminobutyric Acid (D-Dab), or
                      D-2,3-Diaminopropionic Acid (D-Dap), which may be modified
                      with a carboxy-terminal group
SITE                  3..13
                      note = MISC_FEATURE - There is a chemical bond between the
                      side chains of residue 3 and 13
SEQUENCE: 13
ASXLRKLXKR LLX                                                        13

SEQ ID NO: 14         moltype = AA  length = 13
FEATURE               Location/Qualifiers
source                1..13
                      mol_type = protein
                      organism = synthetic construct
VARIANT               1
                      note = Alanine attached to a hydrocarbon group, an aryl
                      group, or a heteroaryl group via a carbonyl group, or
                      attached to nothing
SITE                  8
                      note = MISC_FEATURE - amino iso-butyric acid (Aib)
VARIANT               13
                      note = MISC_FEATURE - halogenated alanine, which may be
                      modified with a carboxy-terminal group
SITE                  3..13
                      note = MISC_FEATURE - There is a chemical bond between the
                      side chains of residue 3 and 13
SEQUENCE: 14
ASCLRKLXKR LLA                                                        13

SEQ ID NO: 15         moltype = AA  length = 13
FEATURE               Location/Qualifiers
source                1..13
                      mol_type = protein
                      organism = synthetic construct
VARIANT               1
                      note = Alanine attached to a hydrocarbon group, an aryl
                      group, or a heteroaryl group via a carbonyl group, or
                      attached to nothing
SITE                  8
                      note = MISC_FEATURE - amino iso-butyric acid (Aib)
VARIANT               13
                      note = MISC_FEATURE - halogenated D-alanine, which may be
                      modified with a carboxy-terminal group
SITE                  3..13
                      note = MISC_FEATURE - There is a chemical bond between the
                      side chains of residue 3 and 13
SEQUENCE: 15
ASCLRKLXKR LLA                                                        13

SEQ ID NO: 16         moltype = AA  length = 13
FEATURE               Location/Qualifiers
source                1..13
                      mol_type = protein
                      organism = synthetic construct
VARIANT               1
```

-continued

```
                        note = Alanine attached to a hydrocarbon group, an aryl
                         group, or a heteroaryl group via a carbonyl group, or
                         attached to nothing
SITE                    3
                        note = MISC_FEATURE - D-Cys
SITE                    8
                        note = MISC_FEATURE - amino iso-butyric acid (Aib)
VARIANT                 13
                        note = MISC_FEATURE - halogenated D-alanine, which may be
                         modified with a carboxy-terminal group
SITE                    3..13
                        note = MISC_FEATURE - There is a chemical bond between the
                         side chains of residue 3 and 13
SEQUENCE: 16
ASCLRKLXKR LLA                                                      13

SEQ ID NO: 17           moltype = AA  length = 13
FEATURE                 Location/Qualifiers
source                  1..13
                        mol_type = protein
                        organism = synthetic construct
VARIANT                 1
                        note = Alanine attached to a hydrocarbon group, an aryl
                         group, or a heteroaryl group via a carbonyl group, or
                         attached to nothing
VARIANT                 3
                        note = MISC_FEATURE - Cys, Glu, Asp, Lys, Ornithine,
                         2,4-Diaminobutyric Acid (Dab), 2,3-Diaminopropionic Acid
                         (Dap), Ser, Gln, halogenated alanine, or their
                         corresponding enantiomeric D-amino acids, or amino
                         iso-butyric acid (Aib)
VARIANT                 8
                        note = MISC_FEATURE - Cys, Glu, Asp, Lys, Ornithine,
                         2,4-Diaminobutyric Acid (Dab), 2,3-Diaminopropionic Acid
                         (Dap), Ser, Gln, halogenated alanine, or their
                         corresponding enantiomeric D-amino acids, or amino
                         iso-butyric acid (Aib)
VARIANT                 13
                        note = MISC_FEATURE - Cys, Glu, Asp, Lys, Orn,
                         2,4-Diaminobutyric Acid (Dab), 2,3-Diaminopropionic Acid
                         (Dap), Ser, Gln, halogenated alanine, or their
                         corresponding enantiomeric D-amino acids, or amino
                         iso-butyric acid (Aib), which may be modified with a
                         carboxy-terminal group
CROSSLNK                3..8
                        note = MISC_FEATURE - Chemical bond between residues 3 and
                         8 is selected from SS-, -CH2-S-CH2 -, -CO-NH-, -CO-O-,
                         -CH2-NH-, -(CH2)n- (n = 2-15), -(CH2)n-CH=CH-(CH2)n- (n =
                         2-15), or -S-(CH2)n -R1-(CH2)n -S-, wherein R1 is a
                         hydrocarbon group, an aryl group or a heteroaryl group, n
                         = 1-3
CROSSLNK                8..13
                        note = MISC_FEATURE - Chemical bond between residues 8 and
                         13 is selected from SS-, -CH2-S-CH2 -, -CO-NH-, -CO-O-,
                         -CH2-NH-, -(CH2)n- (n = 2-15), -(CH2)n-CH=CH-(CH2)n- (n =
                         2-15), or -S-(CH2)n -R1-(CH2)n -S-, wherein R1 is a
                         hydrocarbon group, an aryl group or a heteroaryl group, n
                         = 1-3
SEQUENCE: 17
ASXLRKLXKR LLX                                                      13

SEQ ID NO: 18           moltype = AA  length = 13
FEATURE                 Location/Qualifiers
source                  1..13
                        mol_type = protein
                        organism = synthetic construct
SITE                    1
                        note = Picolinyl alanine
SITE                    8
                        note = amino iso-butyric acid (Aib)
SITE                    13
                        note = Cysteine amide
DISULFID                3..13
                        note = There is a disulfide chemical bond between residue 3
                         and 13
SEQUENCE: 18
ASCLRKLXKR LLC                                                      13

SEQ ID NO: 19           moltype = AA  length = 13
```

-continued

```
FEATURE                 Location/Qualifiers
source                  1..13
                        mol_type = protein
                        organism = synthetic construct
SITE                    1
                        note = Picolinyl alanine
SITE                    8
                        note = amino iso-butyric acid (Aib)
SITE                    13
                        note = Cysteine hydroxymethyl
DISULFID                3..13
                        note = There is a disulfide chemical bond between residue 3
                         and 13
SEQUENCE: 19
ASCLRKLXKR LLC                                                  13

SEQ ID NO: 20           moltype = AA  length = 13
FEATURE                 Location/Qualifiers
source                  1..13
                        mol_type = protein
                        organism = synthetic construct
SITE                    1
                        note = Picolinyl alanine
SITE                    8
                        note = amino iso-butyric acid (Aib)
SITE                    13
                        note = Cysteine aldehyde
DISULFID                3..13
                        note = There is a disulfide chemical bond between residue 3
                         and 13
SEQUENCE: 20
ASCLRKLXKR LLC                                                  13

SEQ ID NO: 21           moltype = AA  length = 13
FEATURE                 Location/Qualifiers
source                  1..13
                        mol_type = protein
                        organism = synthetic construct
SITE                    1
                        note = Picolinyl alanine
SITE                    8
                        note = amino iso-butyric acid (Aib)
VARIANT                 13
                        note = Cysteine modified with an amide, aldehyde, methyl,
                         methoxy, ethoxy, hydroxylamine, methylamine,
                         dimethylamine, ethylamine, aniline, or p-aniline group
DISULFID                3..13
                        note = There is a disulfide chemical bond between residue 3
                         and 13
SEQUENCE: 21
ASCLRKLXKR LLC                                                  13

SEQ ID NO: 22           moltype = AA  length = 13
FEATURE                 Location/Qualifiers
source                  1..13
                        mol_type = protein
                        organism = synthetic construct
SITE                    1
                        note = Picolinyl alanine
SITE                    3
                        note = (4'-pentenyl)alanine
SITE                    8
                        note = amino iso-butyric acid (Aib)
SITE                    13
                        note = (7'-octenyl)alanine amide
SITE                    3..13
                        note = There is a chemical bond between the side chains of
                         residue 3 and 13
SEQUENCE: 22
ASALRKLXKR LLA                                                  13
```